US008263117B2

(12) United States Patent
Ikeda et al.

(10) Patent No.: US 8,263,117 B2
(45) Date of Patent: Sep. 11, 2012

(54) C70-CONTAINING LIPOSOME, METHOD FOR PRODUCING THE SAME, AND USE OF THE SAME

(75) Inventors: Atsushi Ikeda, Ikoma (JP); Jun-ichi Kikuchi, Ikoma (JP)

(73) Assignee: National University Corporation Nara Institute of Science and Technology, Nara (JP)

( * ) Notice: Subject to any disclaimer, the term of this patent is extended or adjusted under 35 U.S.C. 154(b) by 342 days.

(21) Appl. No.: 12/525,977

(22) PCT Filed: Feb. 6, 2008

(86) PCT No.: PCT/JP2008/051928
§ 371 (c)(1),
(2), (4) Date: Aug. 5, 2009

(87) PCT Pub. No.: WO2008/096779
PCT Pub. Date: Aug. 14, 2008

(65) Prior Publication Data
US 2010/0278885 A1    Nov. 4, 2010

(30) Foreign Application Priority Data

Feb. 9, 2007   (JP) .................................. 2007-031340

(51) Int. Cl.
*A61K 9/127*   (2006.01)
(52) U.S. Cl. ....................................................... 424/450
(58) Field of Classification Search .................... 424/450
See application file for complete search history.

(56) References Cited

U.S. PATENT DOCUMENTS

| 7,410,699 | B2 | 8/2008 | Nagasaki et al. |
| 2006/0134095 | A1 | 6/2006 | Ito et al. |
| 2007/0077432 | A1 | 4/2007 | Nagasaki et al. |

FOREIGN PATENT DOCUMENTS

| JP | 7-048302 | 2/1995 |
| JP | 8-143478 | 6/1996 |
| JP | 9-235235 | 9/1997 |
| JP | 2004-022424 | 1/2004 |
| JP | 2006-069812 | 3/2006 |
| JP | 2006-124378 | 5/2006 |
| WO | WO 2004/024455 | 1/2004 |

OTHER PUBLICATIONS

Ikeda et al.; Machine translation of JP 2006-069812 A; published Mar. 16, 2006.*
English translation of Ikeda et al., JP-2006-069812 A, published Mar. 16, 2006, translation dated Aug. 2011 by Schreiber Translations, Inc.*
Derycke, A.S.L. et al., "Liposomes for Photodynamic Therapy," Adv. Drug Deliv. Reviews, vol. 56(1) (Jan. 13, 2004) pp. 17-30.
Ikeda, A. et al., "Induction of cell death by photodynamic therapy with water-soluble lipid-membrane-incorporated [60]fullerene," Organic and Biomolecular Chemistry 2007 Royal Society of Chemistry, vol. 5(8) (2007) pp. 1158-1160.
Supplemental European Search Report dated Feb. 11, 2010 for Application No. EP 08 70 4499.
International Preliminary Report on Patentability dated Jul. 29, 2008 for Application No. PCT/JP2008/051928.
Furuishi, T. et al., "Solubilization of $C_{70}$ into Water by Complexation with δ-Cyclodextrin," Chem. Pharm. Bull., vol. 46(10) (1998) pp. 1658-1659.
International Search Report dated Apr. 8, 2008 for Application No. PCT/JP2008/051928.
Ikeda, A. et al., An extremely effective DNA photocleavage utilizing functionalized liposomes with a fullerene-enriched lipid bilayer, J. Am. Chem. Soc., vol. 129(14) (Mar. 20, 2007) pp. 4140-4141.
Ikeda, A. et al., "Efficient photocleavage of DNA utilizing water-soluble lipid membrane-incorporated [60] fullerenes prepared using a [60] fullerene exchange method," Org. Biomol. Chem., vol. 3(16) (2005) pp. 2907-2909.
Ikeda, A. et al., "New Method for Preparing High Concentration $C_{60}$-incorporated Liposome, and Evaluation of its DNA Photoinduced Cleavage Ability," Polymer Processing, vol. 55 (2006) pp. 180-184.
Ikeda, A. et al., Translation of "New Method for Preparing High Concentration $C_{60}$-incorporated Liposome, and Evaluation of its DNA Photoinduced Cleavage Ability," Polymer Processing, vol. 55 (2006) pp. 180-184.
Komatsu, K., et al., "Aqueous solubilization of crystalline fullerenes by supramolecular complexation with γ-cyclodextrin and sulfocalix[8]arene under mechanochemical high-speed vibration milling," J. Chem. Soc., Perkin Trans., vol, 1 (1999) pp. 2963-2966.
Miyata, N. et al., "Reactive Species Responsible for Biological Actions of Photoexcited Fullerenes," Yakugaku Zasshi, vol. 120(10) (2000) pp. 1007-1016.
Miyata, N. et al., Translation of "Reactive Species Responsible for Biological Actions of Photoexcited Fullerenes," Yakugaku Zasshi, vol. 120(10) (2000) pp. 1007-1016.
Nakanishi, I. et al., "DNA Cleavage via Superoxide Anion Formed in Photoinduced Electron Transfer from NADH to γ-Cyclodextrin-Bicapped $C_{60}$ in an Oxygen-Saturated Aqueous Solution," J. Phys. Chem. B, vol. 106 (2002) pp. 2372-2380.
Wei, X. et al., New chemical method for selective generation of $C_{70}{}^{n-}$ (n=1,2,3) anions and formation and properties of an aqueous colloidal solution of $C_{70}{}^-$, J. Chem. Soc., Perkin Trans. 2, vol. 1 (1999) pp. 121-126.
Yamakoshi, Y. et al., "·OH and $O_2{}^-$ Generation in Aqueous $C_{60}$ and $C_{70}$ Solutions by Photoirradiation: An EPR Study," J. Am. Chem. Soc. vol. 120 (1998) pp. 12363-12364.
Yamakoshi, Y. et al., Active Oxygen Species Generated from Photoexcited Fullerene ($C_{60}$) as Potential Medicines: $O_2{}^-$ versus $^1O_2$, J. Am. Chem. Soc., vol. 125 (2003) pp. 12803-12809.

* cited by examiner

Primary Examiner — Gina C. Yu
Assistant Examiner — Michael B Pallay
(74) Attorney, Agent, or Firm — Frost Brown Todd LLC

(57) ABSTRACT

A solution containing a $C_{70}$ cyclodextrin complex and a solution containing a lipid that is capable of forming a liposome are mixed together at a temperature in a range of 10° C. to 45° C. This produces a $C_{70}$-incorporated liposome which keeps a physical property that the $C_{70}$ fullerene originally has, and is stably solubilized in a polar solvent. Hence, the present invention provides a $C_{70}$-incorporated liposome which keeps a physical property that the $C_{70}$ fullerene originally has, and which is stably solubilized in a polar solvent, a production method of the same, and a use of the same.

3 Claims, 4 Drawing Sheets

(a)

Form I
Uncleaved

▨ Form II
Cleaved

▨ Form III (Linear)
Further cleaved (b)

| Lane | 1 | 2 | 3 | 4 | 5 | 6 |
|---|---|---|---|---|---|---|
| $C_{60}$ | — | — | ○ | ○ | — | — |
| $C_{70}$ | — | — | — | — | ○ | ○ |
| Light | — | ○ | — | ○ | — | ○ |
| Form II + Form III / % | 0 | 1 | 4 | 26 | 4 | 92 |

(c)

(d)

C70-CONTAINING LIPOSOME, METHOD FOR PRODUCING THE SAME, AND USE OF THE SAME

TECHNICAL FIELD

The present invention relates to a liposome incorporating a fullerene, a method for producing the liposome incorporating a fullerene, and use of the liposome incorporating a fullerene. The present invention particularly relates to a liposome incorporating $C_{70}$, a method for producing the liposome incorporating $C_{70}$, and use of the liposome incorporating $C_{70}$.

BACKGROUND ART

Fullerenes have a closed-shell structure consisting of carbon atoms only, and therefore have distinctive properties. Specific examples of the distinctive properties of the fullerenes are that: (1) a π electronic cloud is uniquely delocalized, (2) the fullerene has a high electron affinity, (3) the fullerene has relatively small ionization energy, (4) the fullerene has a high electron accepting capacity, and (5) photoexcitation occurs with visible light. Since the fullerenes have such properties, the fullerenes have been expected to be applicable in a variety of industrial fields, as semiconductor materials, superconductive materials, photoelectric materials, medical materials, cosmetic materials, etc.

For example, in the medical field, use of the fullerenes in photodynamic therapy (hereinafter may be referred to as "PDT") is under consideration. The PDT is a treatment method for cancer and the like; cancer cells or the like are killed with use of active oxygen generated by irradiating light to a photosensitive substance. More specifically, in the PDT, the photosensitive substance is administered to a diseased area, and the diseased area is then irradiated with light so that the active oxygen is generated in the diseased area. The active oxygen, for example singlet oxygen and hydroxyradical, is produced as a result of a photochemical reaction of water and oxygen. The active oxygen or a radical species generated from the active oxygen inhibit activity and multiplication of the cancer cells in the diseased area, so as to destroy the cancer cells. Ultimately, cells such as the cancer cells or the like are killed. Since the fullerenes have the aforementioned distinctive properties, the fullerenes efficiently generate the active oxygen such as the singlet oxygen by irradiation of light. Thus, the application of the fullerenes have been expected in the PDT.

As described above, the fullerenes have been expected to be applicable in a wide range of industrial fields, including application of the fullerenes in medical materials such as the PDT. In a case where the fullerenes are used for a variety of purposes, the fullerenes often need to be dissolved in an intended solvent. For example, in order to use a fullerene in the PDT, the fullerene need to be dissolved in an aqueous solvent. However, the fullerenes are not soluble in a polar solvent, such as water. Non Patent Literature 1 discloses that it is possible to solubilize the fullerene in water by complexing the fullerene with cyclodextrin; however, a cyclodextrin complex of the fullerene is not suitable for practical use due to its extreme thermal instablility. As such, the fullerenes have a disadvantage in that they are usable only with a certain limitation, despite the expectations for use in various fields as described above. In order to overcome such a disadvantage, solubilization of the fullerenes in the aqueous solvent has been studied.

Examples of techniques of the fullerenes solubilization are those disclosed in Patent Literatures 1 to 4, and Non Patent Literature 2. Patent Literature 1 discloses various furalors in which a hydroxyl group is introduced into a carbon atom of fullerene so as to solubilize a fullerene. Patent Literature 2 discloses that it is possible to solubilize the fullerenes by coating a surface of a metal-incorporating fullerene or a salt thereof with a polysaccharide having a functional group selected from the group consisting of a sulfone group, a ketone group, an amino group, and an alkyl group. Further, Patent Literature 3 discloses a method for solubilizing a fullerene by coating the fullerene with a polymer chain. More specifically, Patent Literature 3 discloses a method for solubilizing a fullerene by encapsulating fullerene in a structure composed of (i) a core, which is a polymer chain segment containing a repeat unit with a tertiary amino group and/or a secondary amino group on its side chain and (ii) a shell, which is a poly(ethylene glycol) chain segment. Furthermore, Patent Literature 4 and Non Patent Literature 2 disclose that it is possible to obtain a $C_{60}$-incorporated liposome by transferring $C_{60}$ from a $C_{60}$-cyclodextrin complex into a liposome (by exchange reaction). More specifically, Patent Literature 4 and Non Patent Literature 2 disclose that it is possible to transfer $C_{60}$ into a liposome by mixing a $C_{60}$-cyclodextrin complex into a liposome solution to obtain a mixture and then heating the mixture for 1 to 7 hours with stirring. Moreover, Patent Literature 4 describes that it is possible to solubilize a fullerene through the steps of: preparing a dispersed aqueous solution of the fullerene with use of the fullerene and a dispersion stabilizing agent; and mixing calixarene and the dispersed aqueous solution of the fullerene so as to prepare a complex of calixarene and the fullerene.

Meanwhile, the PDT treats a cancer tissue, in which more water-soluble polymers accumulate than in a normal tissue. The water-soluble polymers once accumulated in the cancer tissue remain for a longer period of time as compared to a case where the water-soluble polymers accumulate in another tissue. Accordingly, when the fullerene is used in the PDT for treating cancer, a fullerene needs not only to be dissolved in an aqueous solvent, but also to be polymerized. Under these circumstances, in order to use the fullerene in the PDT, a technique for polymerizing the fullerene as well as solubilizing the fullerene to an aqueous solvent has been developed. For example, Patent Literature 5 discloses that it is possible to achieve, by chemically-modifying a fullerene with a water-soluble polymer, a solubility of the fullerene to an aqueous solvent as well as an easy transfer of the solubilized fullerene to a cancer tissue.

In addition to the aforementioned technique, a variety of techniques have been disclosed so far for utilizing a fullerene (for example, see Patent Literatures 6 to 9). Patent Literature 6 discloses a new method for stabilizing a diagnostic compound and a therapeutic compound in a cation carrier system. Specifically, Patent Literature 6 discloses a technique that stabilizes, in a cation liposome, a low-molecular-weight compound which has a negative effective charge or a low-molecular-weight compound which is caused to have the negative effective charge due to arbitrary modification. Further, Patent Literature 7 discloses an antioxidant composition and an external composition. Specifically, Patent Literature 7 discloses an antioxidant composition having, as an active constituent, a fullerene included in an organic compound. Furthermore, Patent Literature 8 discloses a technique for solubilizing a fullerene, i.e., a technique for adding higher water solubility to a fullerene. Specifically, Patent Literature 8 discloses a complex of microparticles, which are the fullerenes coated with a polymer chain formed from a certain block copolymer. Patent Literature 9 discloses a photoelectric transducer material in which an electron-accepting compound and an electron-releasing compound respectively form a host-guest complex. Such a complex specifically disclosed in Patent Literature 9 is a complex in which the electron-accepting compound is a fullerene, and the calixarene serves as a host.

CITATION LIST

Patent Literature 1
Japanese Patent Application Publication, Tokukaihei, No. 7-048302 A (Publication Date: Feb. 21, 1995)
Patent Literature 2
Japanese Patent Application Publication, Tokukaihei, No. 8-143478 A (Publication Date: Jun. 4, 1996)
Patent Literature 3
Japanese Patent Application Publication, Tokukai, No. 2005-225772 A (Publication Date: Aug. 25, 2005)
Patent Literature 4
Japanese Patent Application Publication, Tokukai, No. 2006-69812 A (Publication Date: Mar. 16, 2006)
Patent Literature 5
Japanese Patent Application Publication, Tokukaihei, No. 9-235235 A (Publication Date: Sep. 9, 1997)
Patent Literature 6
Japanese Patent Application Publication, Tokukai, No. 2005-534718 A (Publication Date: Nov. 17, 2005)
Patent Literature 7
Japanese Patent Application Publication, Tokukai, No. 2004-250690 A (Publication Date: Sep. 9, 2004)
Patent Literature 8
Japanese Patent Application Publication, Tokukai, No. 2005-225772 A (Publication Date: Aug. 25, 2005)
Patent Literature 9
Japanese Patent Application Publication, Tokukai, No. 2004-022424 A (Publication Date: Jan. 22, 2004)
Non Patent Literature 1
K. Komatsu, K. Fujiwara, Y. Murata and T. Braun, J. Chem. Soc., Perkin Trans. 1, 2963 (1999)
Non Patent Literature 2
A. Ikeda, T. Sato, K. Kitamura, K. Nishiguchi, Y. Sasaki, J. Kikuchi, T. Ogawa, K. Yogo, T. Takeya, Org. Biomol. Chem., 3, 2907-2909 (2005)

SUMMARY OF INVENTION

As described above, solubilization techniques and modification techniques for fullerenes so that a fullerene can be suitably used for specific purposes such as PDT have been developed. However, with the methods disclosed in Patent Literatures 1 to 3, a surface of a fullerene is modified, thereby losing a physical property that the fullerene originally has.

The aforementioned techniques use a $C_{60}$ fullerene as the fullerene in most cases, which $C_{60}$ fullerene can be produced most cheaply and has excellent stability. However, the fullerene differs in physical property depending on the number of carbon atoms. Therefore, all fullerenes can not be solubilized by the same method. Moreover, $C_{70}$ fullerene which includes 70 carbon atoms has a higher light absorbency in a visible light range that is less harmful to a human body, than the $C_{60}$ fullerene which includes 60 carbon atoms. Hence, it is considered that the $C_{70}$ is to be selected for purposes which require high light absorbency.

Thus, there is the need to establish a solubilization technique for each type of fullerene, so that a fullerene having a suitable physical property depending on purpose is desirably selected and used.

The present invention is accomplished in view of this problem, and an object thereof is to provide a $C_{70}$-incorporated liposome in which a physical property that a $C_{70}$ fullerene originally has is kept and which $C_{70}$-incorporated liposome is stably soluble in a polar solvent, a method for producing the $C_{70}$-incorporated liposome, and a use of the $C_{70}$-incorporated liposome.

As a result of diligent study to attain the object, the inventors uniquely found that a $C_{70}$-incorporated liposome can be produced by a simple arrangement of combining a solution that contains a $C_{70}$ cyclodextrin complex and a solution that contains a lipid with which a liposome is formable, at a temperature in a range of 10° C. to 45° C. Based on the finding, the present invention is attained. In Patent Literature 4 which discloses a method for making the fullerene water-based, a $C_{60}$ is made water-based by combining calixarene with a dispersion aqueous solution of a $C_{60}$ fullerene and a dispersing stabilizing agent, in such a manner that a complex of calixarene and the $C_{60}$ is prepared. In this Patent Literature, a cyclodextrin and a liposome are exemplified as the dispersion stabilizing agent. However, the liposome that is used in the technique described in Patent Literature 4 is just a dispersing agent, and Patent Literature 4 does not describe nor suggest an idea to incorporate a $C_{70}$ fullerene in a liposome. Moreover, a technique described in Patent Literature 6 is characterized in that a compound is modified at a part which has a negative effective charge (a part negatively charged). This "modification" includes a denotation of "incorporating a compound to a part which is negatively charged such as the fullerene". Such technique is largely different to the present invention that incorporates the fullerene in the liposome. Organic compounds exemplified in Patent Literature 7 are only organic oligomer, organic polymer, cyclodextrin, crown ether and the like. Patent Literature 7 also has no specific disclosure of an inclusion method. None of Patent Literatures 7 to 9 discloses nor suggests the use of a liposome or including of a $C_{70}$ fullerene in a liposome. Thus, it is easily understood by a person skilled in the art who has read the present specification that the present invention which has been accomplished from originality and ingenuity of the inventors and from a result of trial and error cannot be easily arrived upon from conventional techniques, and is not conventionally expectable.

Namely, the present invention includes the following inventions:

[1] A method for producing a liposome in which a $C_{70}$ fullerene is incorporated, the method including the step of: mixing a first solution and a second solution together at a temperature in a range of 10° C. to 45° C., the first solution containing a $C_{70}$ cyclodextrin complex and the second solution containing a lipid with which a liposome is formable.

[2] The method for producing a $C_{70}$-incorporated liposome according to [1], wherein the $C_{70}$ cyclodextrin complex is at least one of a $C_{70}$ cyclodextrin complex selected from the group consisting of: a $C_{70}$ β-cyclodextrin complex, a $C_{70}$ γ-cyclodextrin complex, a $C_{70}$ δ-cyclodextrin complex, a $C_{70}$ ε-cyclodextrin complex, and a complex between a mono-, di-, or tri-methylated form of β-cyclodextrin, γ-cyclodextrin, δ-cyclodextrin or ε-cyclodextrin and a $C_{70}$ fullerene.

[3] The method for producing a $C_{70}$-incorporated liposome according to [1], wherein the second solution contains at least one lipid selected from the group consisting of lipids represented by the following general formulas (1) to (3):

Chem. 1
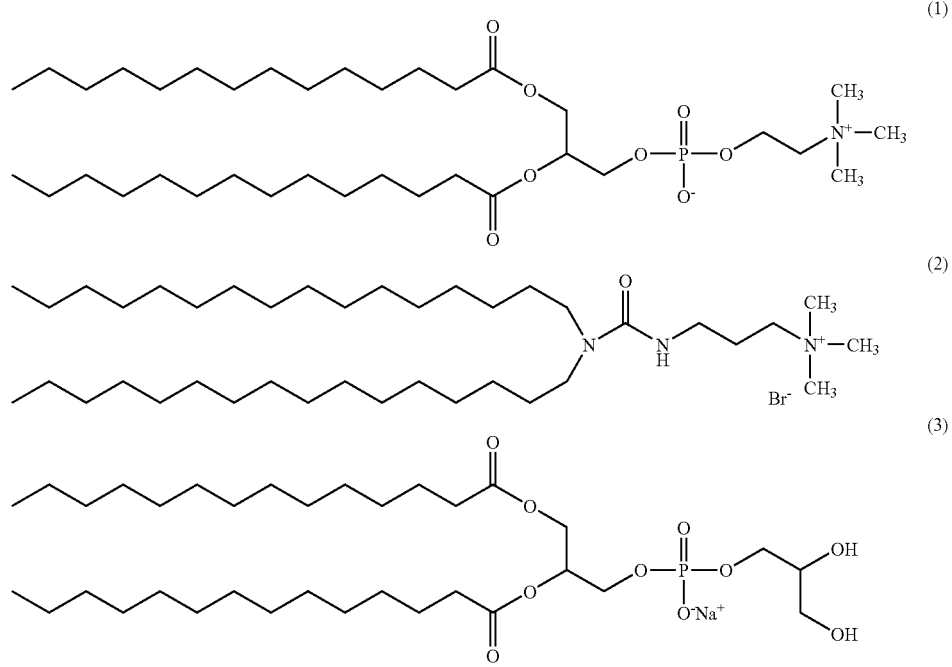
[4] A $C_{70}$-incorporated liposome being a liposome in which a $C_{70}$ fullerene is incorporated.
[5] The $C_{70}$-incorporated liposome according [4], wherein the liposome includes at least one lipid selected from the group consisting of lipids represented by the following general formulas (1) to (3):
Chem. 2
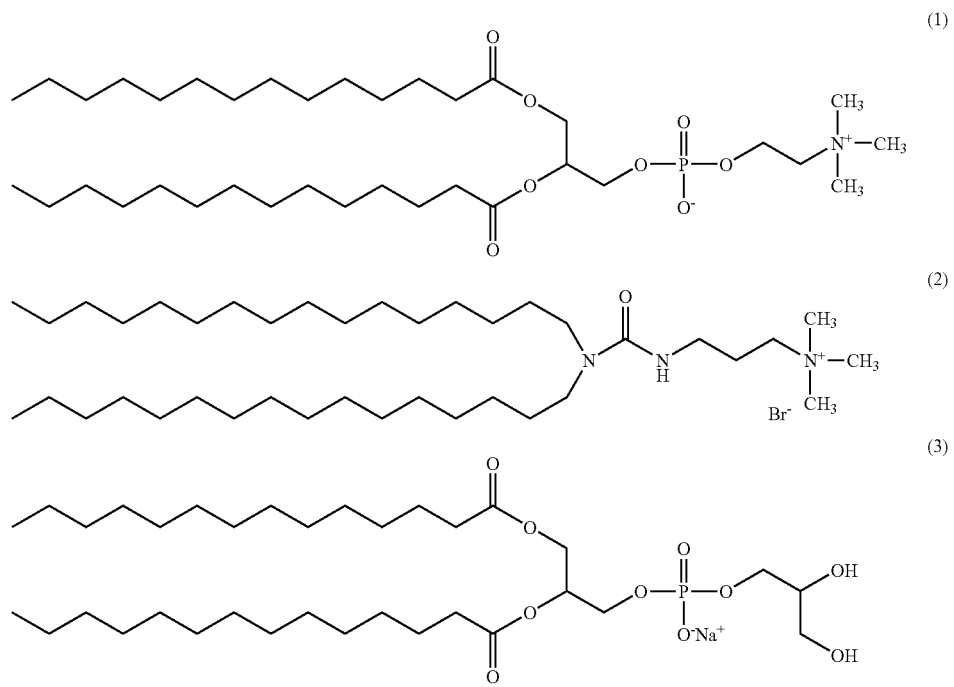

[6] The $C_{70}$-incorporated liposome according to [4], generating active oxygen due to irradiation of light that has a wavelength in a range of 350 nm to 800 nm.

[7] The $C_{70}$-incorporated liposome according to [4], wherein $C_{70}$ is incorporated in a range of 0.1 mol % to 20 mol % with respect to a whole amount of lipid constituting the liposome.

[8] A composition including a $C_{70}$-incorporated liposome as set forth in any one of [4] to [7].

[9] The composition according to [8], wherein the composition is used for photodynamic therapy.

[10] The composition according to [9], wherein an object to be treated by the photodynamic therapy is selected from the group consisting of: a cancer cell, an age-related macular degeneration, an atherosclerosis lesion, an articular rheumatism lesion, an intractable verrucosis, an acne vulgaris, and a papillomavirus.

[11] The composition according to [10], wherein the age-related macular degeneration is of an exudative type.

[12] The composition according to claim 8, including the $C_{70}$-incorporated liposome in a range of 2 mol % to 20 mol %.

[13] A photodynamic therapy method comprising the steps of: applying to a diseased part a $C_{70}$-incorporated liposome as set forth in any one of claims 4 to 7; and irradiating light to the diseased part.

For a fuller understanding of the nature and advantages of the invention, reference should be made to the ensuing detailed description taken in conjunction with the accompanying drawings.

BRIEF DESCRIPTION OF DRAWINGS

FIG. 1 is an explanatory view schematically illustrating a structure of a $C_{70}$-incorporated liposome in accordance with one embodiment of the present invention.

FIG. 2 is an explanatory view showing UV-vis absorption spectra of (i) a $C_{70}$-incorporated liposome in accordance with Examples of the present invention and (ii) a conventional $C_{60}$-incorporated liposome.

In FIG. 3, (a) is a view illustrating a structure of a typical plasmid, and (b) to (d) are views showing experimental results of DNA cleavage abilities for a $C_{70}$-incorporated liposome in Examples of the present invention.

FIG. 4 is an explanatory view showing experimental results of cell killing abilities for (i) a $C_{70}$-incorporated liposome in Examples of the present invention and (ii) a conventional $C_{60}$-incorporated liposome.

In FIG. 5, (a) is an explanatory view showing a $C_{70}$-incorporated liposome aqueous solution produced by a method in Examples of the present invention for producing a $C_{70}$-incorporated liposome, and (b) is an explanatory view showing a $C_{70}$-incorporated liposome aqueous solution produced by a method in accordance with Reference Example for producing a $C_{70}$-incorporated liposome.

FIG. 6 is an explanatory view illustrating UV-vis absorption spectra of the $C_{70}$-incorporated liposome aqueous solutions shown in (a) and (b) of FIG. 5.

DESCRIPTION OF EMBODIMENTS

The following description explains one embodiment of the present invention. The present invention is not limited to this embodiment.

<I. $C_{70}$-Incorporated Liposome>

Figure 1:
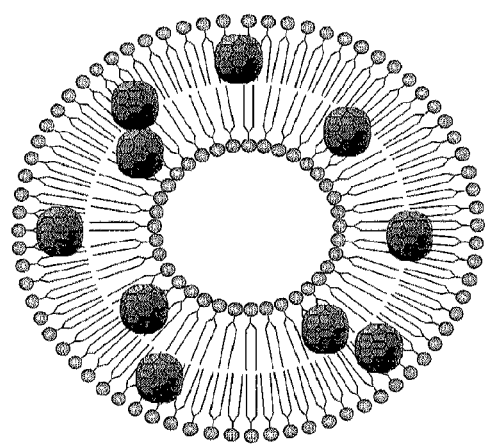
FIG. 1

A $C_{70}$-incorporated liposome in accordance with the present invention is a liposome that incorporates $C_{70}$ fullerene (hereinafter may be referred to simply as "$C_{70}$"), as illustrated in FIG. 1. In a $C_{70}$-incorporated liposome in accordance with the present invention, the $C_{70}$ with an unmodified surface is present inside a liposome. Hence, the $C_{70}$ is solubilized to an aqueous solvent while a physical property that the $C_{70}$ originally has is kept. As a result, the $C_{70}$-incorporated liposome is widely applicable to technical fields which desirably use a water-soluble $C_{70}$. FIG. 1 illustrates a liposome in which the $C_{70}$ is embedded within a liposome membrane, as one embodiment of a $C_{70}$-incorporated liposome in accordance with the present invention. However, the present invention is not limited to this structure. That is to say, in the present specification, a "$C_{70}$-incorporated liposome" denotes (a) a liposome in which the $C_{70}$ is present in an aqueous phase (inner aqueous phase) confined in an inside part of a liposome membrane, (b) a liposome in which the $C_{70}$ is embedded in a liposome membrane, and (c) a liposome in which part of the $C_{70}$ is present in the inside aqueous phase and the rest of the $C_{70}$ is embedded within the liposome membrane. Moreover, with the $C_{70}$-incorporated liposome in accordance with the present invention, the $C_{70}$ may be present as a single molecule, without the $C_{70}$ interacting with each other, or the $C_{70}$ may be present as an association of a plurality of $C_{70}$ molecules. Furthermore, the $C_{70}$ may be present in such a manner that just a part of the molecules of the $C_{70}$ is associated with each other.

In the present specification, "aqueous solvent" denotes a water-based solvent. Further, "liposome" denotes a structure including a liposome membrane with a lipid bilayer. The lipid bilayer is a bilayer made of lipid molecules, and has the same structure as a cell membrane. The lipid molecules have a hydrophilic part, which favors a polar solvent such as water, and a hydrophobic part, which favors a nonpolar solvent such as oil. In the lipid bilayer, the lipid molecules are aligned in two layers with their hydrophobic parts faced to each other, and the hydrophilic parts facing outside of the bilayer.

A specific composition of a liposome with the $C_{70}$-incorporated liposome in accordance with the present invention is not particularly limited. In the liposome, any of a cationic lipid, an anionic lipid and a neutral lipid may be used in combination. In other words, the liposome does not necessarily require containing all of a cationic lipid, an anionic lipid and a neutral lipid, and may be a liposome that contains a certain one type or two types of lipid. In the present invention, it is possible to obtain a $C_{70}$-incorporated liposome in which a property of the $C_{70}$ is usable as desired, by altering the composition of the liposome.

For instance, the $C_{70}$ is known as having a property that generates active oxygen caused by light irradiation. In order to prepare a $C_{70}$-incorporated liposome with such $C_{70}$ property, it is preferable for the liposome to contain a cationic lipid, and is further preferable for the liposome to contain cationic cholesterol. With this structure, it is possible to obtain a stable $C_{70}$-incorporated liposome that can generate active oxygen due to light irradiation, which $C_{70}$-incorporated liposome does not decompose due to an effect caused by the active oxygen.

Moreover, a $C_{70}$-incorporated liposome containing the cationic lipid attains excellent cell permeability. Such a $C_{70}$-incorporated liposome which generates active oxygen and has excellent cell permeability is suitable for use in photodynamic therapy (hereinafter also referred to as "PDT"). In the present specification, the "active oxygen" is not particularly limited, and denotes a singlet oxygen and a hydroxyl radical, for example.

Moreover, the $C_{70}$ has an activity to scavenge active oxygen. In order to obtain a $C_{70}$-incorporated liposome added with such a $C_{70}$ property, it is preferable to use, for instance, a liposome which is described in Japanese Patent Publication No. 2006-124378 A1 or the like. With this structure, it is possible to obtain a $C_{70}$-incorporated liposome which can efficiently scavenge active oxygen in an aqueous solvent.

Examples of a neutral lipid included in the liposome encompass: 1,2-dioleoyl-sn-glycelo-3-phosphoethanolamine (DOPE), phosphatidylcholine, phosphatidylserine, phosphatidylglycerol, phosphatidylinositol, phosphatidylethanolamine, phosphatidic acid, dipalmitoylphosphatidylcholine (DPPC), distearoylphosphatidylcholine (DSPC), dimyristolylphosphatidylcholine (DMPC), dioleoylphosphatidylcholine (DOPC), dipalmitoylphosphatidylglycerol (DPPG), distearoylphosphatidylserine (DSPS), distearoylphosphatidylglycerol (DSPG), dipalmitoylphosphatidylinositol (DPPI), distearoylphosphatidylinositol (DPSI), dipalmitoylphosphatidic acid (DPPA), distearoylphosphatidic acid (DSPA), cardiolipin, sphingomyelin, egg yolk lecithin, soy lecithin, lysolecithin, any one of these being hydrogenated by a predetermined method (e.g., hydrogenated soy lecithin), and phospholipids of hydroxides and the like. Moreover, in the present invention, a lipid represented by the following general formula (1) is suitably used as a neutral lipid:

Chem. 3

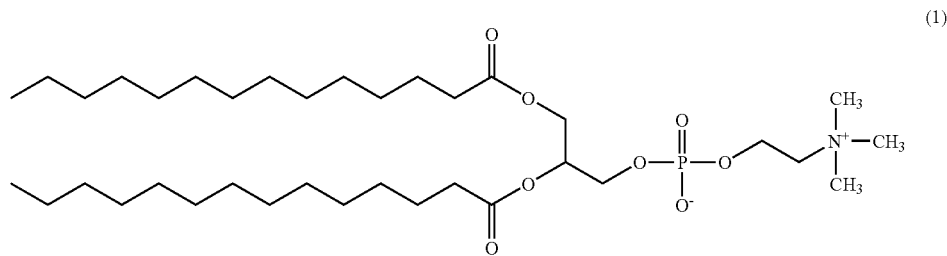

(1)

Examples of an anionic lipid included in the liposome encompass: anionic phospholipids having saturated or unsaturated linear or branched C10 to C30 fatty acid residue of dimyristoylphosphatidylglycerol, dipalmitoylphosphatidylglycerol, phosphatidylglycerols derived from natural substances such as egg yolk or soy, a completely hydrogenated phosphatidylglycerol, distearoylphosphadylglycerol or the like. Moreover, in the present invention, a lipid represented by the following general formula (3) is suitably used as an anionic lipid:

Chem. 4

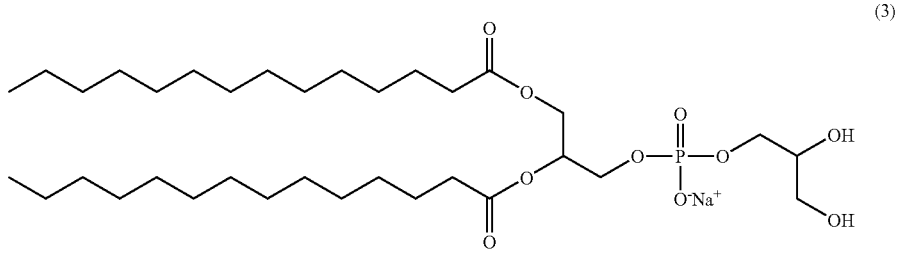

(3)

Such a $C_{70}$-incorporated liposome is suitably used in fields of foods, medicine, cosmetics and the like.

The following description explains more specifically of a lipid included in the liposome.

Examples of the cationic lipid included in the liposome emcompass cationic lipids such as: 1,2-dioleoyloxy-3-(trimethylammonium)propane (DOTAP), N,N-dioctadecylamido glycyl spermine (DOGS), dimethyl dioctadecyl ammonium bromide (DDAB), 3β[N-(N7,N'-dimethylamino-ethane)-carbamoyl] cholesterol, stearylamine, N-(α-trimethylammonioacetyl)dodecyl-D-glutamate chloride, N-[1-(2,3-oleoyloxy)propyl]-N,N,N-trimethylammonium chloride (DOTMA), 2,3-dioleoyloxy-N-[2-(spermine carboxamido) ethyl]-N,N-dimethyl-1-propanammonium trifluoroacetate (DOSPA), N-[1-(2,3-dimyristyloxy)propyl]-N,N-dimethyl-N-(2-hydroxy ethyl) ammonium bromide (DMRIE), and 1,2-dioleoyl-3-dimethylammonium propanediol (DODAP). Furthermore, cationic phospholipids such as an ester of a phosphatidic acid and aminoalcohol, for instance an ester of a diparmitoylphosphatidic acid (DPPA) or a distearoylphosphatidic acid (DSPA) and hydroxyethylene diamine may also be used. Moreover, in the present invention, a lipid represented by the following general formula (5) is suitably used as a cationic lipid:

Chem. 5

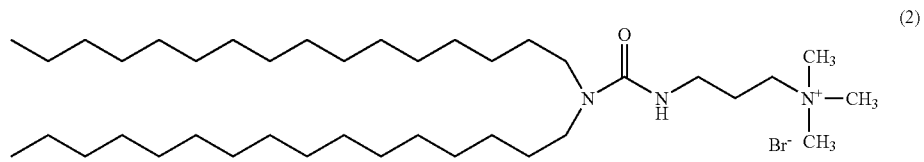

(2)

With the cationic lipid, it is possible to obtain a $C_{70}$-incorporated liposome having an average particle diameter in a range of 50 nm to 200 nm. A $C_{70}$-incorporated liposome with such an average particle diameter allows selectively targeting cancer cells with use of an EPR (Enhanced permeability and retention) effect.

When a cationic lipid is contained in the $C_{70}$-incorporated liposome in accordance with the present invention, its amount contained is preferably not more than 90 mol %, more preferably not more than 50 mol %, and further preferably not more than 20 mol %, with respect to a whole amount of lipid.

In the present invention, the liposome may solely include a lipid among the lipids exemplified above, or may include a plurality of such lipids in combination. Moreover, when a liposome contains a plurality of charged lipids (anionic lipids or cationic lipids) in combination, it is preferable to contain negatively charged lipids in combination, or positively charged lipids in combination. In this way, it is possible to prevent the $C_{70}$-incorporated liposomes from bonding together, thereby reducing aggregation of the $C_{70}$-incorporated liposome. Moreover, when a neutral lipid and a charged lipid are contained in combination, a neutral lipid:charged lipid ratio (molar ratio) is preferably in a range of 200:1 to 1:9, is more preferably in a range of 100:1 to 1:1, and is further preferably in a range of 40:1 to 5:1.

The following description explains an embodiment in which a plurality of lipids are used in combination, with reference to a specific example. Cationic lipid is known to have cell permeability. Therefore, in a case where the $C_{70}$-incorporated liposome in accordance with the present invention is used for treatment such as PDT and the like, the $C_{70}$-incorporated liposome preferably contains a cationic lipid. On the other hand, the cationic lipid is generally known to be toxic. Therefore, an amount of the cationic lipid contained is determined upon consideration of the cell permeability and any side effects caused by the toxicity. In this case, it is preferable to adjust the amount of the cationic lipid contained by using the neutral lipid and the cationic lipid in combination. Thus, by use of the neutral lipid and the cationic lipid in combination, and by appropriately adjusting the amount of cationic lipid contained to be in the aforementioned range, it is possible to produce a $C_{70}$-incorporated liposome that has good cell permeability and which causes less side effects caused by the toxicity.

Moreover, the $C_{70}$-incorporated liposome in accordance to the present invention may contain a glycolipid. Examples of the glycolipid encompass: glycerolipids such as digalactosyl diglyceride and galactosyl diglyceride sulfate, and sphingoglycolipids such as galactosylceramide, galactosylceramide sulfate, lactosylceramide, ganglioside G7, ganglioside G6, and ganglioside G4.

The $C_{70}$-incorporated liposome in accordance with the present invention may contain components other than the $C_{70}$ and the lipids. More specifically, the $C_{70}$-incorporated liposome may contain sterols which act as a membrane stabilizing agent. Examples of the sterols encompass: cholesterol, dihydrocholesterol, cholesterol ester, phytosterol, sitosterol, stigmasterol, campesterol, cholestanol, and lanosterol. Moreover, sterol derivatives such as 1-O-sterolglycoside, 1-O-sterolmaltoside, or 1-O-sterolgalactoside may be contained as a stabilizing agent. In a case where the $C_{70}$-incorporated liposome in accordance with the present invention contains the sterols, its amount contained is preferably in a range of 0.05 mol % to 70 mol %, is more preferably in a range of 0.1 mol % to 60 mol %, and is further preferably in a range of 0.5 mol % to 40 mol %, with respect to the whole amount of lipid molecules. The sterols contained in the aforementioned ranges allow stabilization of the $C_{70}$-incorporated liposome without inhibiting formation of the $C_{70}$-incorporated liposome. Moreover, when the $C_{70}$-incorporated liposome contains cholesterol, the cholesterol also may act as an anchor for introducing polyalkylene oxide. Various functional substances can be immobilized to an end of a polyalkylene chain by covalent bonding.

Moreover, the $C_{70}$-incorporated liposome in accordance with the present invention may contain a glycol. Examples of the glycol encompass: ethylene glycol, diethylene glycol, triethylene glycol, propylene glycol, dipropylene glycol, trimethylene glycol, and 1,4-butanediol. Its contained amount is preferably in a range of 0.01 mol % to 20 mol %, and is more preferably in a range of 0.5 mol % to 10 mol %, with respect to the whole lipid amount of the $C_{70}$-incorporated liposome. With this structure, it is possible to effectively retain water-soluble substances inside the $C_{70}$-incorporated liposome. Moreover, the $C_{70}$-incorporated liposome in accordance with the present invention may contain a dialkyl phosphate such as dicetyl phosphate that is a negatively charged substance, and may contain an aliphatic amine or the like such as stearylamine as a compound that provides positive charge.

Furthermore, the $C_{70}$-incorporated liposome in accordance with the present invention may have, on its particle surface, a substituent for adding a specific function, or may have a molecule for adding a specific function, the molecule being added onto or inserted into the particle surface. Examples of the substituent and molecules encompass: a substituent and molecule for allowing the $C_{70}$-incorporated liposome to target a specific organ or tissue in a case where the $C_{70}$-incorporated liposome is administered to a living body, and a substituent and molecule for improving stability of the $C_{70}$-incorporated liposome in the living body to which the $C_{70}$-incorporated liposome is administered. More specifically, a polyalkylene oxide (PAO) group that is a polymer chain (polyoxy alkylene chain), or a phospholipid or a compound having a similar group may be given as an example of a molecule for improving the stability of the $C_{70}$-incorporated liposome. Attachment of the PAO group or the polyethylene glycol (PRG) chain to a surface of the $C_{70}$-incorporated liposome gives the $C_{70}$-incorporated liposome a greater stability. Moreover, by appropriately modifying a length of an oxyethylene unit of a PEG group represented by $—(CH_2CH_2O)_n—H$ and a proportion of the PEG group to be introduced, it is possible to adjust the function for improving stability of the $C_{70}$-incorporated liposome. The PEG group is preferably a PEG group having 10 to 3500 oxyethylene units, and more preferably 100 to 2000 oxyethylene units. When the $C_{70}$-incorporated liposome in accordance with the present invention incorporates the PEG, its amount incorporated is preferably in a range of 0.1 mol % to 30 mol %, and is more preferably in a range of 1 mol % to 15 mol %, with respect to the whole amount of lipid in the $C_{70}$-incorporated liposome. Note that a well-known technique for incorporating the PEG in the liposome may be used to incorporate the PEG into the $C_{70}$-incorporated liposome.

Moreover, when the $C_{70}$-incorporated liposome includes a PAO group represented by $-(AO)_n—Y$ (in the general formula, AO is a C2 to C4 oxyalkylene group; n is an average added molecular amount of the oxyalkylene group; and Y is a hydrogen atom, an alkyl group or a function-adding functional group). Here, n in the general formula is preferably in a range of 1 to 2000, more preferably in a range of 10 to 500, and further preferably in a range of 20 to 200. Examples of the C2 to C4 oxyalkylene group encompass: an oxyethylene group, an oxypropylene group, an oxytrimethylene group, an oxy-1-ethylethylene group, and an oxy-1,2-dimethylethylene group.

Moreover, when n in the aforementioned general formula is not less than 2, oxyalkylene groups may be identical, or may be different oxyalkylene groups. When the oxyalkylene groups are different, they may be present randomly or in blocks. Moreover, in a case where the PAO group is hydrophilic, it is preferable that the oxyalkylene groups are ethylene oxide solely, further preferably with $n \geq 10$ in the aforementioned formula. When different types of alkylene oxide are to be added, it is preferable that ethylene oxide be added by not less than 20 mol %, and it is more preferable that the ethylene oxide be added by not less than 50 mol %. In a case where the PAO group is lipophilic, ethylene oxide is added preferably fewer in mol than other oxyalkylene groups. For example, it is preferable that the oxyalkylene group be a block copolymer of polyethylene oxide and polypropylene oxide.

Moreover, a C1 to C5 aliphatic carbon hydroxide group (may be branched) may be given as an example of the alkyl group indicated by Y in the general formula. The "function-adding functional group" denotes a substituent for adding a "functional substance" such as sugar, glycoprotein, an antibody, lectin, or a cell adhesion factor at an end of the PAO group. More specifically, substitutes which is highly reactive such as an amino group, an oxycarbonyl imidazole group, and an N-hydroxy succinimide group may be given as examples of the substituent. A $C_{70}$-incorporated liposome to which a PAO group having the aforementioned functional substance attached at its end is fixed, has the function of the functional substance in addition to the effect caused by the PAO group. The function of the functional substance may be, for example an effect as a "recognition element" such as directivity or recognition of cancer cells. Moreover, when the $C_{70}$-incorporated liposome contains a phosphatide or compound that includes a PAO group, the phosphatide or the compound may be of a sole type or may be of a combination of a plurality of types. Moreover, the amount of the phosphatide or the compound contained is preferably in a range of 0.001 mol % to 50 mol %, more preferably in a range of 0.01 mol % to 25 mol %, and further preferably in a range of 0.1 mol % to 10 mol %, with respect to a whole constituent of the $C_{70}$-incorporated liposome. The PAO group may be introduced into the $C_{70}$-incorporated liposome by a conventionally well-known technique.

The $C_{70}$-incorporated liposome in accordance with the present invention is not particularly limited in its size. More specifically, the $C_{70}$-incorporated liposome is designable to have a size suitable for usage thereof. For example, when the $C_{70}$-incorporated liposome is to be used as a tumor treating drug in which the $C_{70}$-incorporated liposome selectively targets cancer tissues by an EPR effect, it is preferable that the $C_{70}$-incorporated liposome have an average particle diameter in a range of 50 nm to 200 nm, more preferably in a range of 60 nm to 200 nm, and particularly preferably in a range of 70 nm to 150 nm. Moreover, in a case where the $C_{70}$-incorporated liposome is directly applied to the cancer tissue via a catheter extended to a blood vessel near a cancer focus, on the basis of arterial injection chemotherapy which is regional chemotherapy, it is preferable that the $C_{70}$-incorporated liposome have an average particle diameter preferably in a range of 500 nm to 1.0 µm, more preferably in a range of 700 nm to 900 nm, further preferably in a range of 750 nm to 850 nm, and particularly preferably around 800 nm. Having such an average particle diameter allows the $C_{70}$-incorporated liposome to directly reach the target cancer cell even if the $C_{70}$-incorporated liposome is dispersed inside an arteria nutricia which has an increased permeability, without the $C_{70}$-incorporated liposome leaking from a cinclis of the blood vessel which leads to the cancer cell.

In the present invention, the amount of the $C_{70}$ incorporated in the $C_{70}$-incorporated liposome is not particularly limited. The amount of the $C_{70}$ incorporated in the $C_{70}$-incorporated liposome may be changed as desired, as explained in a later-described method for producing the $C_{70}$-incorporated liposome. Change of the amount of the $C_{70}$ incorporated allows modification to the property of the $C_{70}$-incorporated liposome. This is more specifically explained as follows. In a case where the $C_{70}$ is associated in the $C_{70}$-incorporated liposome, changing the amount of the $C_{70}$ incorporated changes the associated state of the $C_{70}$ in the $C_{70}$-incorporated liposome. Therefore, what is expected is not just simply the change in the property due to the change in the amount of the $C_{70}$ contained, but also a change in property due to the change in the associated state. Hence, it is preferable to appropriately change the amount of the $C_{70}$ contained in the $C_{70}$-incorporated liposome depending on usage of the $C_{70}$-incorporated liposome. For example, in a case where the $C_{70}$-incorporated liposome is used for PDT use, it is preferable for the $C_{70}$-incorporated liposome to contain the $C_{70}$ in a range of 0.1 mol % to 20 mol % and more preferably in a range of 0.5 mol % to 15 mol %, with respect to the whole amount of lipid. Such an arrangement allows an increase in the amount of active oxygen generated per $C_{70}$-incorporated liposome molecule due to irradiation of light. As such, it is possible to attain the PDT effect with just a small amount of $C_{70}$-incorporated liposome.

The $C_{70}$-incorporated liposome in accordance with the present invention has a structure as described above. Hence, the $C_{70}$-incorporated liposome is soluble to an aqueous solvent. Moreover, the physical property of the $C_{70}$-incorporated liposome can be controlled as desired, for example by the average particle diameter, the amount of the $C_{70}$ incorporated, a composition of a liposome, and additions of another component. Therefore, the $C_{70}$-incorporated liposome in accordance with the present invention may be used for various purposes, with respect to its physical property. More specifically, in one embodiment, a $C_{70}$-incorporated liposome in accordance with the present invention has a property to generate active oxygen due to irradiation of light. Such a $C_{70}$-incorporated liposome has high light activity, and can generate a lot of active oxygen by excitation due to light which has a wavelength in a range from 350 nm to 700 nm. Hence, such a $C_{70}$-incorporated liposome is suitably used for purposes such as PDT, microorganism-killing effect, disinfection, sterilization, and other such purposes. Moreover, such a $C_{70}$-incorporated liposome may be used for cleaving DNA, for example as a research reagent. "Light activity" in the present specification denotes an activity that is excited by irradiation of light, and preferably denotes an activity in which active oxygen is generated by irradiation of light. Moreover, as one embodiment, the $C_{70}$-incorporated liposome in accordance with the present invention has a property to scavenge active oxygen. Such a $C_{70}$-incorporated liposome is widely used for purposes which require scavenging active oxygen.

<II. Composition Including $C_{70}$-incorporated Liposome>

Moreover, as one embodiment, the present invention provides a composition that includes the aforementioned $C_{70}$-incorporated liposome in accordance with the present invention. A composition in accordance with the present invention is not particularly limited in its specific structures, as long as the aforementioned $C_{70}$-incorporated liposome is included therein. For example, a solution which has the $C_{70}$-incorporated liposome melted in an aqueous solvent is included in a composition in accordance with the present invention. Moreover, way of use for the solution in accordance with the present invention is also not particularly limited. The following description explains, as one embodiment of a composition in accordance with the present invention, a pharmaceutical composition, a microorganism-killing composition, and a cosmetic composition, however the present invention is not limited to these examples.

(A) Pharmaceutical Composition

A composition in accordance with the present embodiment includes a $C_{70}$-incorporated liposome which generates active oxygen due to light irradiation, preferably light irradiation by use of light having a wavelength in a range from 350 nm to 800 nm, and more preferably light irradiation by use of light having a wavelength in a range from 350 nm to 700 nm. More specifically, the $C_{70}$-incorporated liposome preferably incorporates $C_{70}$ with a liposome that contains a cationic lipid. As the cationic lipid, a cationic lipid exemplified above may be contained for example. However, among the exemplified cationic lipids, it is preferable to contain a lipid represented by the aforementioned general formula (2). Moreover, its amount contained is preferably in a range from 1 mol % to 50 mol %, and is more preferably 10 mol %, with respect to a whole amount of lipid.

Furthermore, in the present embodiment, it is preferable that the liposome include a neutral lipid in addition to the cationic lipid. As for the neutral lipid, a neutral lipid as exemplified above may be contained for example, however among the exemplified neutral lipids, it is preferable to contain the lipid represented by the aforementioned general formula (1). Its amount contained is preferably in a range of 50 mol % to 99 mol %, and more preferably around 90 mol %, with respect to the whole amount of lipid. In other words, one preferable embodiment of the $C_{70}$-incorporated liposome which is included in a composition in accordance with the present embodiment is, a $C_{70}$-incorporated liposome which includes 10 mol % of a lipid represented by the aforementioned general formula (2), and includes 90 mol % of a lipid represented by the aforementioned general formula (1), with respect to the whole lipid amount.

The amount of the $C_{70}$-incorporated liposome included in a composition in accordance with the present embodiment is not particularly limited, however is preferably in a range of 2 mol % to 20 mol %, and more preferably in a range of 5 mol % to 15 mol %. More specifically, a composition in accordance with the present embodiment may contain a component that is pharmaceutically acceptable, other than the $C_{70}$-incorporated liposome. Examples of such components encompass: various buffers physiologically acceptable; chelating agents of edetic acids such as EDTA $Na_2$—Ca and EDTA $Na_2$; pharmacologically active substances (e.g., vasolidators, coagulation-inhibiting agent); further an osmoregulating chemical, a stabilizing agent, an antioxidant (e.g., α-tocopherol, ascorbic acid), viscosity modifying agent, and a preservative. Saline (0.9 salt water) for instance is an example of the osmoregulating chemical. Moreover, an amine buffer and a carbonate buffer are examples of a pH buffer.

The composition in accordance with the present embodiment may be used for PDT. In this case, a method for administering the composition in accordance with the present embodiment is not particularly limited, and is administered by, for instance, hypodermic injection or intravenous injection to the diseased part, or by performing a surgical procedure to the diseased part. Moreover, when the composition in accordance with the present embodiment is used for the PDT, the composition is (i) first administered to the diseased part, then (ii) this diseased part is left for a predetermined time in an environment that does not expose the diseased part to light, and thereafter (iii) light is irradiated to the diseased part for a predetermined time. The wavelength of the light is not particularly limited for the irradiation, however is preferably in a range of 350 nm to 800 nm, and is more preferably in a range of 350 nm to 700 nm. Use of the light with such wavelength allows efficient irradiation of light to the diseased part. How the light is irradiated is not particularly limited; the light can be irradiated by use of various light sources such as an artificial diffuse light or a laser. More specifically, examples of preferable light sources are a halogen lamp, a xenon lamp, and a metal halide lamp. Among these lamps, it is preferable to use the metal halide lamp, as a light source that has a radiant intensity spectrum strong against visible light. It is also possible to use, as the light source, light-emitting elements such as LED and organic EL elements.

Moreover, when a composition in accordance with the present embodiment is used for PDT, an object to be treated is not particularly limited. For example, the composition may be used for treatment against cancer cells, age-related macular degeneration, atherosclerosis lesions, articular rheumatism lesions, intractable verrucosis, acne vulgaris, and papillomavirus. Among these, the composition is suitably used for treatment against cancer cells and age-related macular degeneration. A type of cancer cell is not particularly limited, and it is possible to use the composition against various cancer cells. Moreover, the age-related macular degeneration is a disorder that a part in the retina called the macula that has a cell which identifies color degenerates due to aging; among the age-related macular degeneration, the composition in accordance with the present embodiment is suitably used for treatment against age-related macular degeneration of a "exudative type" caused by choroidal neovascularization.

(B) Microorganism-killing Composition

A composition in accordance with the present embodiment includes a $C_{70}$-incorporated liposome that generates active oxygen due to light irradiation, preferably due to light irradiation having a wavelength in a range of 350 nm to 800 nm, and more preferably having a wavelength in a range of 350 nm to 700 nm. An amount of the $C_{70}$-incorporated liposome included in the composition is not particularly limited, as long as microorganisms and the like can be sterilized by the active oxygen that is generated by the $C_{70}$-incorporated liposome due to light irradiation. How the composition in accordance with the present embodiment is specifically used is also not particularly limited. For example, the composition in accordance with the present embodiment may be dispersed to a part in which microorganisms exist, and thereafter be exposed to natural sunlight at a region on which the composition was dispersed, or light may be irradiated to the region for a predetermined time with use of an artificial light. In a case where light is irradiated by use of the artificial light, it is preferable to irradiate a light from which ultraviolet light is cut out by use of a filter or the like.

Moreover, the microorganism to be killed is not particularly limited, in a case where it is to be carried out by use of the composition in accordance with the present embodiment. For example, the composition may be used for sterilization or antimicrobial process against bacteria such as *Escherichia coli, Pseudomonas aeruginosa,* or *Salmonella*. It is also possible to use the composition for removing or preventing generation of mold such as *Cladosporium* (*Aspergillus niger*) or *aspergillus*.

(C) Cosmetic Composition

A composition in accordance with the present embodiment includes a $C_{70}$-incorporated liposome that is capable of scavenging active oxygen. The composition in accordance with the present invention preferably includes other compounding ingredients for cosmetics along with the $C_{70}$-incorporated liposome. Examples of the other compounding ingredients encompass: a gelatinizing agent, an ultraviolet absorbing agent, an antibacterial agent, a pH adjusting agent, extracts of an animal or plant origin and extracts of a microorganism origin, vitamins, amino acids, nucleic acid-related substances, hormone, an enzyme, a blood circulation accelerating agent, a dermal astringent, and an antiseborrheic agent.

Examples of the gelatinizing agent encompass: amino acid derivatives such as N-lauroyl-L-glutamic acid and α,γ-di-n-butylamine; dextrine fatty acid esters such as dextrine palmitate, dextrine stearate, and dextrine 2-ethylhexanoate palmitate; sucrose fatty acid esters such as sucrose palmitate and sucrose stearate; benzylidene derivatives of sorbitol such as monobenzylidene sorbitorl and dibenzylidene sorbitol; and organomodified clay mineral such as dimethyl benzyl dodecyl ammonium montmorillonite clay and dimethyl dioctadecyl ammomium montmorillonite clay.

Examples of the ultraviolet absorbing agent encompass: cinnamic acid-based ultraviolet absorbing agents such as 2-ethylhexyl p-methoxycinnamate, isopropyl p-methoxycinnamate, p-methoxyhydrocinnamate diethanolamine salt, glyceryl mono-2-ethylhexanoate di-p-methoxycinnamate, octyl methoxycinnamate, and methyl diisopropylcinnamate; benzophenone-based ultraviolet absorbing agent such as 2-hydroxy-4-methoxybenozophenone, 2-hydroxy-4-methoxybenzophenone-5-sulfuric acid, 2-hydroxy-4-methoxybenzophenone-5-sodium sulfate, 2,4-dihydroxybenzophenone, 2,2'-dihydroxybenzophenone, 2,2',4,4'-tetrahydroxybenzophenone, and 2-hydroxy-4-n-octoxybenzophenone; benzoic acid-based ultraviolet absorbing agents such as p-aminobenzoic acid, ethyl p-aminobenzoate, butyl p-aminobenzoate, 2-ethylhexyl p-dimethylaminobenzoate, glyceryl p-aminobenzoate, and amyl p-aminobenzoate; salicylic acid-based ultraviolet absorbing agents such as 2-ethylhexyl salicylate, triethanolamine salicylate, homomenthyl salicylate, dipropylene glycol salicylate, methyl salicylate, ethylene glycol salicylate, phenyl salicylate, amyl salicylate, benzyl salicylate, isopropylbenzyl salicylate, and potassium salicylate; dibenzoylmenthane-based ultraviolet absorbing agents such as 4-t-butyl-4'-methoxydibenzoylmethane, 4-isopropyl-dibenzoylmethane, 4-methoxybenzoylmethane, and 4-t-butyl-4'-hydroxydibenzoylmethane; anthranilic acid-based ultraviolet absorbing agent such as methyl-O-aminobenzoate, 2-phenyl-benzimidazole-5-sulfuric acid, 2-phenyl-5-methylbenzoxazole, 3-(4-methylbenzylidene)camphor, 2-ethylhexyl-2-cyano-3,3-diphenylacrylate, 2-ethyl-2-cyano-3,3'-diphenylacrylate, 2-(2'-hydroxyl-5-methylphenyl)benzotriazole, and menthyl anthranilate; urocanic acid-based ultraviolet absorbing agents such as ethyl urocanate; titanium oxide, zirconium oxide, and cerium oxide.

Examples of the antibacterial agent encompass: benzoic acid, sodium benzoate, salicylic acid, phenol, sorbic acid, potassium sorbate, p-hydroxybenzoate, p-chlormetacresol, hexachlorophene, benzalkonium chloride, chlorhexidine chloride, trichlorocarbanilide, photosensitive principle, bis (2-pyridyltio-1-oxide)zinc, pentadiol, iturin, surfactin, polyglycin, ethanol, phenoxyethanol, and isopropyl phenol.

Examples of the pH adjusting agent encompass: lactic acid, citric acid, glycolic acid, succinic acid, tartaric acid, malic acid, potassium carbonate, sodium hydrogen carbonate, and ammonium hydrogencarbonate, and examples of a refrigerant encompass L-menthol, and campher.

Extracts of animal or plant origin and extracts of microorganism origin encompass: extracts of animal origin, of mammals, birds, fish, molluscas, shellfish, insects and the like, such as blood extract of swine , bovine, and the like, serum-removed protein extract, spleen extract, constituent of an avian's egg, cockscomb extract, fish meat extract, squid ink, chitin, chitosan, shell extract, shell meat extract, royal jelly, silk protein and their resolvents or their derivatives, hemoglobin or its derivative, milk, casein and its derivatives or its resolvent, lactoferrin or its resolvent, collagen and its derivative or its hydrolysate, elastin and its derivative or its hydrolysate, keratin and its derivative or its resolvent; extracts of microorganism origin such as yeast metabolite, fermentation metabolite, yeast extract, lactic bacterium extract, bifidobacterium extract, and the like, glabridin, glabrene, liquiritin, isoliquiritin, and *Glycyrrhiza* extract including these, placenta extract, carotinoids and animal and plant extracts including these, neoagarobiose, agarose saccharide, asparagus extract, *Polygonum bistorta* extract, *Pisum savitum* extract, *Rosa multiflora* fruit extract, *Scutellaria baicalensis* root extract, *Ononis spinosa* extract, seaweeds extract, *Rubus idaeus* fruit extract, sophora root extract, *Millettia reticulata* extract, *Eleutherococcus senticosus* extract, vegetable oil including linoleic acid, asarum sieboldi extract, *Crataegus cuneata* extract, *Cassia Mimosoides* extract, white lily extract, peony root extract, *Inula britannica* extract, mulberry root extract, soy extract, tea extract, *Angelica acutiloba* root extract, molasses extract, white lotus extract, beech extract, grape seed extract, *Flodemannita* extract, humulus lupulus extract, *Rosa rugosa* extract, Mokka (*Chaenomeles lagenariakoidz*) extract, saxifrage extract, *Coix* seed extract and Luo Han Guo extract, *Asparagus officinalis, Rubia argyi, Vitis vinifera, Mallotus japonicus, Akebia quinata, Cannabis, Ipmoea nil, Vigna angularis, Gambir, Hydrangea macrophylla var. thunbergii, Gynostemma pentaphyllum, Reynoutria japonica, Ficus carica, Ginkgo biloba, Cananga odorata, Prunella vulgaris subsp. asiatica, Prunus mume, Arctostaphylsos uva-ursi, Citrus unshiu, Eleutherococcus senticosus, Senna obtusifolia, Styphnolobium japonicum, Pisum sativum, Plantago asiatica, Abelmoschus esculentus, Inula britannica var. japonica, Juglans mandashurica var. sachalinensis, Patrinia scabiosaefolia, Fragaria chiloensis var. ananassa, Diospyros kaki, Glechoma hederacea var. grandis, Polygonum multiflorum, Anacardium occidentalis, Valeriana fauriei, Trichosanthes cucumeroides, Chaenomeles sinensis, Paullinia cupana, Platycodon grandiflorum, Chrysanthemum morifolium var. sinense, Catalpa ovata, Rumex japonicus, Gymnema sylvestre, Agrimonia pilosa var. japonica, Psidium guajava, Lycium chinense, Pueraria lobata, Cinnamomum camphora, Castanea crenata, Millettia reticulata, Laurus nobilis, Cinnamomi cortex, Rubus chingii Hu., Piper nigrum, Coffea spp., Scrophularia buergeriana, Jateorhiza columba, Camelia sasanqua, Zanthoxylum puiperitum, Crocus sativus, Prunus spp., Punica granatum, Sophora subprostrata, Cassia mimosides, Aster tataricus, Acrus calamus, Citrullus vulgaris, Stevia, Prunus salicina, Hedera helix, Pyrus communis, Achillea millefolium, Juniperus communis var. communis, Armoracia rusticana, Acorus gramineous, Oenanthe javanica, Senega Virginia, Cassia senna, Rheum officinale, Citrus aurantium, Tamarindus indica, Aralia elata, Taraxacum, Cichorium intybus, Eugenia caryophyllata, Schisandra chinensis, Polyporus, Oenothera tetraptera, Centella asiatica, Commelina communis, Tetragonia tetragonoides, Juglans regia var. orientalis, Benincasa cerifera, Eucommia ulmoides, Hibiscus manihot, Caosella bursa-pastoris, Citrus natsudaidai, Nandina domestica, Picrasma quassioides, Achillea sibirica, Ananas comosus, Hibiscus, Carica papaya, Ocimum basilicum, Nelumbo nucifera, Hordeum vulgare L. var nudum Hook. f., Belamcanda chinensis, Arachis hypogaea, Isodon japonicus, Trapa japonica, Pistacia vera, Thujopsis dolabrata, Agaricus blazei, Angelica dahurica, Eribotrya japonica, Tussilago farfara, Rhus javanica, Eupatoriumfortunei, Vaccinum* spp., *Siler divaricatum, Physalis aklekengi* var. *francheti, Magnolia obovata, Chaenomeles lagenaria, Rosa maikwai, Ephedra sinica, Mangifera indica, Ganoderma lucidum, Bupleurum falcatum* var. *komarowi, Lythrum anceps, Cryptotaenia japonica, Mimosa, Melilotus officinalis, Cucumis melo, Magnolia liliflora, Momordica grosvenori, Corchorus olitorius, leguminosae, Alpina oxyphylla, leonurus sibiricus, Rodgersia podophylla*, palm, *Alnus firma fruit, Viscum album* var. *coloratura, Persicaria hydropiper, Phytolacca esculenta, Myrica rubra, Daphyniphyllum macropodum, Artemisia princeps, Secale cereale, Orchidaeceae, Euphoria longana, Malus pumila, Litchi chinensis*, and *Forsythia suspensa*.

Examples of vitamins encompass: vitamin F such as linolenic acid and its derivatives; vitamin K such as phytonadione, menaquinone, menadione, and menadiol; vitamin P such as eriocitrin and hesperidin; and other vitamins such as biotin, carnitine and ferulic acid.

Examples of amino acids encompass: amino acids and their derivatives and their salts, which examples of the amino acids are glycine, alanine, valine, isoleucine, serine, threonine, aspartic acid, glutamic acid, asparagine, glutamine, lysine, hydroxylysine, arginine, cystine, methionine, phenylalanine, tyrosine, proline, hydroxyproline, ornithin, citrulline, and theanine, or amino acid derivatives of pyrrolidone carbonic acid or the like or their derivatives.

Examples of the nucleic acid-related substances encompass: deoxyribonucleic acid and its salt, adenylic acid derivative and their salt, which adenylic acid derivative is selected from the group consisting of: adenosine triphosphate, adenosine diphosphate, and adenosine monophosphate, cyclic AMP, cyclic GMP, flavin adenine dinucleotide, guanine, adenine, cytosine, thymine, xanthine, and caffeine and theophylline which are their derivatives, and their salts.

Examples of the hormones encompass estradiol, and ethenyl estradiol. Furthermore, examples of the enzymes encompass lipase and papain.

Examples of the blood circulation accelerating agent encompass: nonanoic acid vanillylamide, capsaicin, zingerone, Cantharides tincture, ichthammol, α-borneol, inositol hexanicotinate, cyclandelate, cinnarizine, tolazoline, acetylcholine, Verapamil, cepharantin, and γ-oryzanol. Moreover, examples of the dermal astringent encompass tannic acid, and examples of the antiseborrheic agent encompass sulfur, and Thiatrol™.

Moreover, the composition in accordance with the present embodiment is not particularly limited in its shape, and may be in powder, bulk, paste, solution, fluid dispersion, film, or gel form.

<III. Method for Producing $C_{70}$-incorporated Liposome>

A method in accordance with the present invention for producing the $C_{70}$-incorporated liposome is suitably used for producing the aforementioned $C_{70}$-incorporated liposome in accordance with the present invention. The following description explains one embodiment of a method in accordance with the present invention for producing the $C_{70}$-incorporated liposome. Prior to this description is an explanation of a process which lead to the invention of the method in accordance to the present invention for producing the $C_{70}$-incorporated liposome.

Patent Literature 4 and Non Patent Literature 2 each disclose a method for producing a $C_{60}$-incorporated liposome, in which a solution containing a cyclodextrin complex of a $C_{60}$ fullerene (hereinafter referred to just "$C_{60}$") and a solution containing a lipid that is capable of forming a liposome are mixed together, which mixed solution is heated to be at a temperature in a range of 70° C. to 80° C. for several hours while the solution is stirred. The $C_{60}$ has a property such that the $C_{60}$ has difficulty in self-association as compared to the $C_{70}$. The other way round, $C_{70}$ self-associates more easily than $C_{60}$. It is considered that a fullerene becomes difficult to be introduced in the liposome once the fullerene is self-associated. Therefore, it has been assumed that it would be difficult to introduce the $C_{70}$ into the liposome with the methods disclosed in Patent Literature 4 and Non Patent Literature 2. There are also conventionally no cases where a $C_{70}$-incorporated liposome has been produced. Under such circumstances, the inventors of the present invention experimented the production of a $C_{70}$-incorporated liposome in conformity with the method disclosed in Patent Literature 4 and Non Patent literature 2. As a result, it was possible to produce a $C_{70}$-incorporated liposome, however problems arose such that an introduction rate of the $C_{70}$ into the liposome is poor, and that the liposome results to have a large particle diameter. Upon this, the inventors carried out diligent study, thereby uniquely finding that a $C_{70}$-incorporated liposome in which the aforementioned problems are solved is producible in such a short time of less than one minute by mixing, at a temperature in a range of 10° C. to 45° C., a first solution containing a cyclodextrin complex of the $C_{70}$ and a second solution containing a lipid that is capable of forming a liposome.

Based on this finding, the inventors of the present invention attained the present invention.

Namely, a method in accordance with the present invention for producing a $C_{70}$-incorporated liposome is not particularly limited in any structures, used equipment, used apparatuses or the like, as long as the method includes a step of mixing (hereinafter referred to also as "mixing step") a first solution and a second solution together in a temperature range from 10° C. to 45° C., wherein the first solution contains a $C_{70}$ cyclodextrin complex and the second solution contains a lipid that is capable of forming a liposome. For example, the method in accordance with the present invention for producing the $C_{70}$-incorporated liposome, as an embodiment, may include a step of modifying (hereinafter may be referred to as "modification step") the $C_{70}$-incorporated liposome in such a manner that a substituent is introduced to a surface of the $C_{70}$-incorporated liposome for adding a specific function, or a lipid is inserted to a surface of the $C_{70}$-incorporated liposome for adding a specific function. More specifically, the modification step includes a manipulation step required for producing the $C_{70}$-incorporated liposome that has the structure explained in the foregoing <I. $C_{70}$-incorporated Liposome>. In the present specification, "modification of the $C_{70}$-incorporated liposome" denotes a chemical or a physical modification to the $C_{70}$-incorporated liposome. Moreover, the modification step is not limited to be carried out after the mixing step, and may be carried out before the mixing step or simultaneously with the mixing step.

Moreover, the method in accordance with the present invention for producing the $C_{70}$-incorporated liposome, as one embodiment, may include a step of purifying (hereinafter may be referred to as "purification step") the $C_{70}$-incorporated liposome. In the mixing step, an aqueous solution which contains the $C_{70}$-incorporated liposome is produced. The purification step allows: separation of the $C_{70}$-incorporated liposome from the aqueous solution; dissolving this separated $C_{70}$-incorporated liposome into another solvent; and removal of impurities (precipitate and deposit) from the aqueous solution produced in the mixing step.

The following description specifically explains the mixing step.

The mixing step mixes the first solution and the second solution together at a temperature in a range of 10° C. to 45° C. How to mix the first solution and the second solution together is not particularly limited, as long as the first solution and the second solution is mixed together and an even solution is obtained.

The first solution may include other components, as long as the solution includes at least a $C_{70}$ cyclodextrin complex. The $C_{70}$ cyclodextrin complex is soluble in an aqueous solvent, however lacks stability against heat, thereby not being frequently applied in the industrial fields. The inventors took this unstableness of the $C_{70}$ cyclodextrin complex as an advantage, and were successful in producing a stable and practical $C_{70}$-incorporated liposome. How the $C_{70}$ cyclodextrin complex is produced is not particularly limited, however is producible via a method disclosed in Non Patent Literature 1. Moreover, a cyclodextrin included in the $C_{70}$ cyclodextrin complex is not particularly limited. Examples of the cyclodextrin encompass: β-cyclodextrin, γ-cyclodextrin, δ-cyclodextrin, ε-cyclodextrin, and their methylated cyclodextrins. In other words, the $C_{70}$ cyclodextrin complex in the present invention is a $C_{70}$ cyclodextrin complex selected from the group consisting of: a $C_{70}$ β-cyclodextrin complex, a $C_{70}$ γ-cyclodextrin complex, a $C_{70}$ δ-cyclodextrin complex, a $C_{70}$ ε-cyclodextrin complex, and a complex between a mono-, di-, or tri-methylated form of β-cyclodextrin, γ-cyclodextrin, δ-cyclodextrin, or ε-cyclodextrin and a $C_{70}$ fullerene. Among these $C_{70}$ cyclodextrin complexes, the $C_{70}$ γ-cyclodextrin complex is preferably used. The exemplified $C_{70}$ cyclodextrin complex may be used solely or in combination. By selecting a different type(s) of $C_{70}$ cyclodextrin complex, it is possible to produce various types of $C_{70}$-incorporated liposomes that have different physical properties.

The second solution is not particularly limited in its structure as long as the solution is an aqueous solution that contains a lipid that is capable of forming a liposome. In other words, the solution may include components other than the lipid that is capable of forming a liposome. Such components include a component for modifying a $C_{70}$-incorporated liposome thus obtained. More specifically, components exemplified in the foregoing <I. $C_{70}$-incorporated Liposome> may be included in the second solution. By containing such a component, it is possible to add a specific function to the $C_{70}$-incorporated liposome thus obtained.

The lipid may be any of the cationic lipid, the anionic lipid, and the neutral lipid, and these lipids may also be used in combination. That is to say, it is possible to use the lipids exemplified in the foregoing <I. $C_{70}$-incorporated Liposome> in combination as appropriate. Modification of the composition for the lipid in the second solution allows controlling a physical property of the $C_{70}$-incorporated liposome thus obtained as desired. For example, containing a cationic lipid in the second solution improves an absorption efficiency (cell permeability) of the $C_{70}$-incorporated liposome to a cell. Furthermore, upon irradiation of light to the $C_{70}$-incorporated liposome, active oxygen generated from the $C_{70}$ is discharged outside the $C_{70}$-incorporated liposome with the fear of damaging the liposome. Moreover, use of the liposome which includes a lipid represented by the foregoing general formula (1) and (2) allows production of a $C_{70}$-incorporated liposome that has an average particle diameter with which a cancer cell is efficiently targeted with use of an EPR effect.

In the second solution, the lipid may be in the form of a liposome, or the liposome may be formed in the mixing step.

Moreover, a concentration of the $C_{70}$ cyclodextrin complex in the first solution and a concentration of the liposome in the second solution are not particularly limited, as long as the concentrations are in a range in which the preparation of the $C_{70}$-incorporated liposome is possible. A mixing ratio of the first solution and the second solution is also not particularly limited, and is appropriately set so that an amount of the $C_{70}$ incorporated in the produced $C_{70}$-incorporated liposome is a desired amount. That is to say, in the method according to the present invention for producing $C_{70}$-incorporated liposome, the amount of the $C_{70}$ incorporated in the $C_{70}$-incorporated liposome is desirably controlled by adjusting a molecular ratio between the $C_{70}$ cyclodextrin complex and the lipid which are to be mixed together. According to the method in accordance with the present invention for manufacturing the $C_{70}$-incorporated liposome, an exchange reaction occurs substantially completely. Hence, for example, when the first solution and the second solution are mixed together in such amounts that 10 mol of a lipid is present per 1 mol of a $C_{70}$ cyclodextrin complex, this produces a $C_{70}$-incorporated liposome which incorporates $C_{70}$ of an amount 10 mol % with respect to the lipid. When the amount of the $C_{70}$ contained in the $C_{70}$-incorporated liposome changes, an association state of the $C_{70}$ changes in the $C_{70}$-incorporated liposome. Thus, with the $C_{70}$-incorporated liposome in accordance with the present invention, it is possible to produce a $C_{70}$-incorporated liposome in which a physical property such as a light property is desirably controlled.

As described above, a method in accordance with the present invention for producing a $C_{70}$-incorporated liposome includes the aforementioned structure. This allows a $C_{70}$-incorporated liposome to be formed immediately after (specifically in one minute from) mixing the first solution and the second solution together. As a result, it is possible to produce the $C_{70}$-incorporated liposome with good production efficiency. Moreover, according to the structure, a process such as heating is not required. Hence, it is possible to produce the $C_{70}$-incorporated liposome at low costs with no limitations caused by equipment. Furthermore, according to the structure, a composition of the liposome and the amount of $C_{70}$ incorporated are modifiable as desired. This allows production of a $C_{70}$-incorporated liposome that has a desired physical property, such as a $C_{70}$-incorporated liposome that has excellent stability against active oxygen, a $C_{70}$-incorporated liposome that efficiently scavenge active oxygen, or a $C_{70}$-incorporated liposome with which a cancer cell can be targeted with use of the EPR effect.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

EXAMPLES

The present invention is more specifically described with reference to Examples and FIGS. 2 to 6. However, the present invention is not limited to such Examples and Figures. A person skilled in the art may change, correct, and modify the present invention in many variations, provided such variations do not exceed the scope of the present invention.

Production Example 1

Production of $C_{70}$ γ-cyclodextrin Complex

First, 5.0 mg of $C_{70}$ was treated with 8 molar equivalents of γ-cyclodextrin (61 mg) under a high-speed vibration for 20 minutes to obtain a mixture of the $C_{70}$ and the γ-cyclodextrin. The mixture thus obtained was treated with 1.5 ml of water, thereby obtaining a red-brown aqueous solution. The red-brown aqueous solution was diluted to ⅕, and its UV-vis absorption spectrum was measured. The measured UV-vis absorption spectrum was substantially the same to that of the $C_{70}$ dissolved in cyclohexane. The original red-brown aqueous solution was diluted so that a concentration thereof was $2 \times 10^4 M$. Here, the concentration was calculated by using a molecular extinction coefficient of the red-brown aqueous solution at 831 nm ($\epsilon_{381} = 3.80 \times 10^4$ cm$^2$g$_{-1}$).

Example 1

Production of $C_{70}$-incorporated Liposome

A $C_{70}$-incorporated liposome was produced with use of the $C_{70}$ γ-cyclodextrin complex produced in Production Example 1. Specifically, first, 2.0 mM lipid solution (lipid represented by Formula (1): 90 mol %, lipid represented by Formula (2): 10 mol %) was added to 0.20 mM $C_{70}$ γ-cyclodextrin complex solution (1 ml) at room temperature (25° C.) and mixed with each other, thereby obtaining an aqueous solution of the $C_{70}$-incorporated liposome.

A γ-cyclodextrin concentration, a $C_{70}$ concentration, and a lipid concentration in the $C_{70}$ γ-cyclodextrin complex solution were individually evaluated by use of integral intensities of NMR spectrum. The results were such that: the γ-cyclodextrin concentration was 1.9 mM; the $C_{70}$ concentration was 0.1 mM; and the lipid concentration was 1.0 mM. In other words, γ-cyclodextrin:$C_{70}$:lipid (molar ratio) was 1.9:0.1:1.0.

A change from the $C_{70}$ γ-cyclodextrin complex to the $C_{70}$-incorporated liposome was confirmed by a change in the US-vis absorption spectrum. Further, the $C_{70}$ concentration in the $C_{70}$-incorporated liposome obtained was equal to an initial concentration of the $C_{70}$ γ-cyclodextrin complex solution. That is, it was found that all the $C_{70}$ contained in the $C_{70}$ γ-cyclodextrin complex were transferred to the liposome. Therefore, the $C_{70}$-incorporated liposome produced in the present Example contained the $C_{70}$ in an amount of 10 mol % with respect to the lipid.

The UV-vis absorption spectrum of the $C_{70}$-incorporated liposome was measured with use of the aqueous solution of the $C_{70}$-incorporated liposome thus obtained, and compared with that of a $C_{60}$-incorporated liposome. The $C_{60}$-incorporated liposome was produced in accordance with a method described in Non Patent Literature 2.

Figure 2:
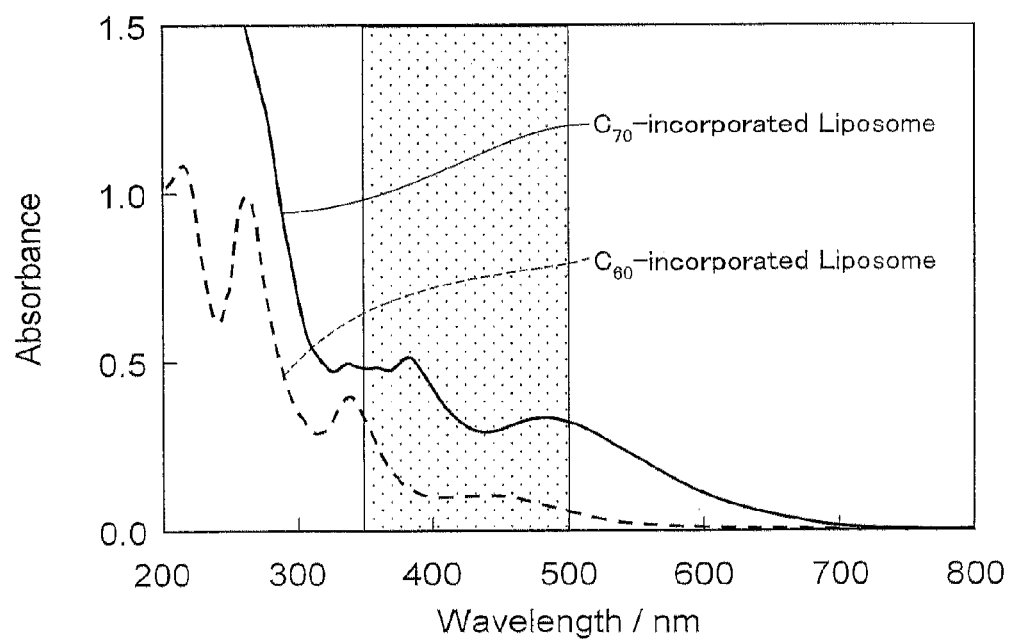
FIG. 2

As a result, as shown in FIG. 2, the $C_{70}$-incorporated liposome exhibited higher absorbance than the $C_{60}$-incorporated liposome in every wavelength region, especially in a 350 nm to 700 nm wavelength region.

Example 2

DNA Cleavage Effect of $C_{70}$-incorporated Liposome

A DNA cleavage effect of the $C_{70}$-incorporated liposome produced in Example 1 was studied by using a ColE 1 supercoiled plasmid (hereinafter may be referred to as "plasmid") as DNA. As shown in (a) of FIG. 3, the plasmid exists in a supercoiled state in which duplex is not at all cleaved (Form I in (a) of FIG. 3), in a non-supercoiled circular state resulting from cleavage of the duplex (Form II in (a) of FIG. 3), or in a linear state resulting from further cleavage of the duplex (Form III in (a) of FIG. 3). In Example 2, an experiment was carried out to study how much percentage of the Form I plasmids were cleaved and converted to Form II or Form III.

In the experiment, a percentage (cleaved percentage) of the plasmids being cleaved and converted to Form II or Form III was evaluated by: (1) adding nothing to the ColE1 supercoiled plasmid (Form I, concentration in a reaction solution was 1.3 mg/l), (2) just irradiating the plasmid with light, (3) just adding the $C_{60}$-incorporated liposome (concentration in a reaction solution was 30 μM) to the plasmid, (4) adding the $C_{60}$-incorporated liposome (concentration in a reaction solution was 30 μM) to the plasmid to obtain a mixture and irradiating the mixture with light, (5) just adding the $C_{70}$-incorporated liposome (concentration in a reaction solution was 30 μM) to the plasmid, or (6) adding the $C_{70}$-incorporated liposome (concentration in a reaction solution was 30 μM) to the plasmid to obtain a mixture and irradiating the mixture with light. Thereby, a ratio of cleavage (cleaved percentage) caused by Form II or Form III was evaluated. Light irradiation was carried out at a distance of 10 cm by use of a 500 W xenon lamp (UI-502Q; Ushio, Inc) at 25° C. for 3 hours under an aerobic condition. The cleaved percentage was evaluated through a method as described below. First, 10% SDS and a sample buffer (Wako Pure Chemical Industries, Ltd.) were added in this order to a sample having been subjected to the above process. Next, the sample was subjected to electrophoresis with use of 0.9 agarose gel. Then, the agarose gel having been subjected to the electrophoresis was stained with SYBR Gold (1:10000 diluted; Molecular Probes Inc.), and was observed on a UV transilluminator. The cleaved percentage was calculated by analyzing an image observed with use of the UV transilluminator.

Figure 3:
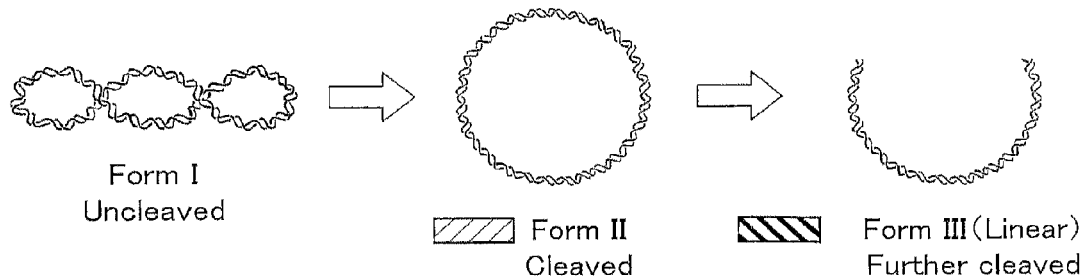
FIG. 3
Figure 3:
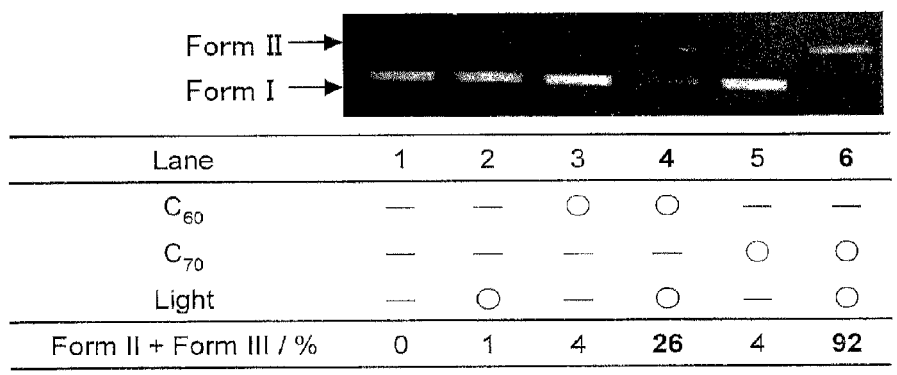
Figure 3:
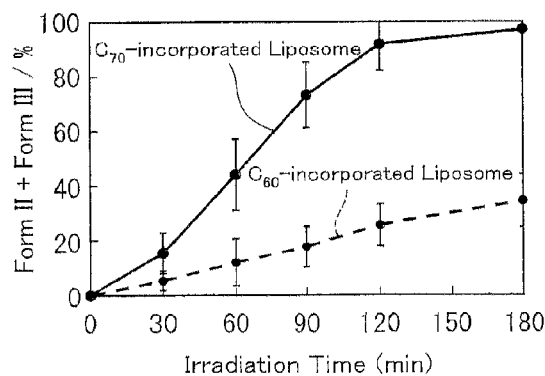
Figure 3:
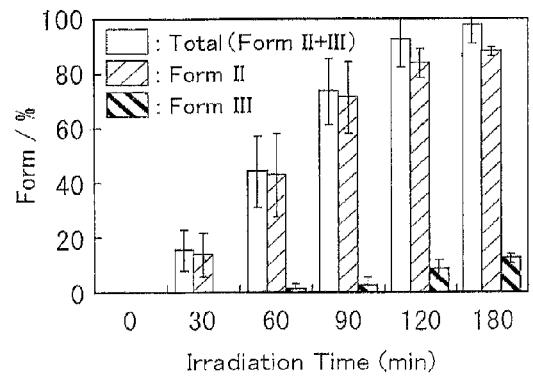

As a result, as shown in (b) of FIG. 3, the plasmids were not at all cleaved in the case where (1) nothing was added to the plasmid. Further, only a few plasmids were cleaved in the cases where (2) the plasmid was just irradiated with light, (3) just the $C_{60}$-incorporated liposome was added to the plasmid, and (5) just the $C_{70}$-incorporated liposome was added to the plasmid. In contrast, the plasmids were cleaved in the cases where (4) the $C_{60}$-incorporated liposome was added to the plasmid to obtain a mixture and the mixture was irradiated with light and (6) the $C_{70}$-incorporated liposome was added to the plasmid to obtain a mixture and the mixture was irradiated with light. The cleaved percentage was much higher in the case where (6) the $C_{70}$-incorporated liposome was added to the plasmid to obtain a mixture and the mixture was irradiated with light as compared to the case where (4) the $C_{60}$-incorporated liposome was added to the plasmid to obtain a mixture and the mixture was irradiated with light: 90% of the plasmid was cleaved for the case (6) and 26% of the plasmid was cleaved for the case (4). That is, only approximately one-fourth of the DNAs were cleaved in the case where (4) the $C_{60}$-incorporated liposome was added to the plasmid to obtain a mixture and the mixture was irradiated with light.

Further, comparison between a DNA photocleavage by the $C_{70}$-incorporated liposome and a DNA photocleavage by the $C_{60}$-incorporated liposome was carried out over time after initiation of light irradiation. The result was as follows. As shown in (c) of FIG. 3, 90% or more of the DNAs were cleaved by the $C_{70}$-incorporated liposome in about 2 hours, whereas only approximately 30% of the DNAs were cleaved by the $C_{60}$-incorporated liposome even after 3 hours. Furthermore, a level of the DNA photocleavage by the $C_{70}$-incorporated liposome was studied. The result was such that, as shown in (d) of FIG. 3, a percentage of the DNAs being cleaved and converted to Form III increased as a light irradiation period increased.

The above experiment revealed that the $C_{70}$-incorporated liposome has a much higher DNA photocleavage ability than the $C_{60}$-incorporated liposome.

Example 3

Photodynamic Activity of $C_{70}$-incorporated Liposome Against HeLa Cell

An experiment was carried out to evaluate a photodynamic activity, against a HeLa cell, of the $C_{70}$-incorporated liposome produced in Example 1. In the experiment, the $C_{60}$-incorporated liposome was also evaluated in the same manner, so as to perform comparison between the $C_{70}$-incorporated liposome and the $C_{60}$-incorporated liposome.

Figure 4:
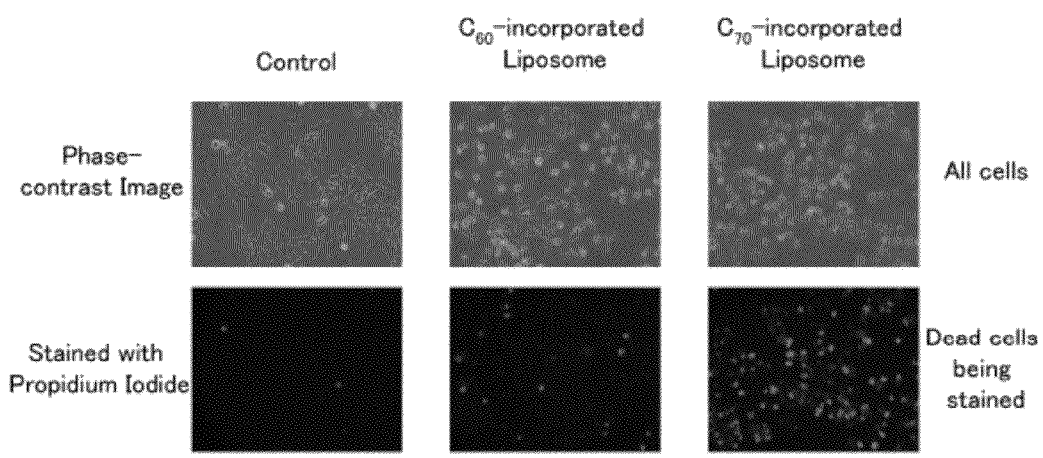
FIG. 4
Figure 5:
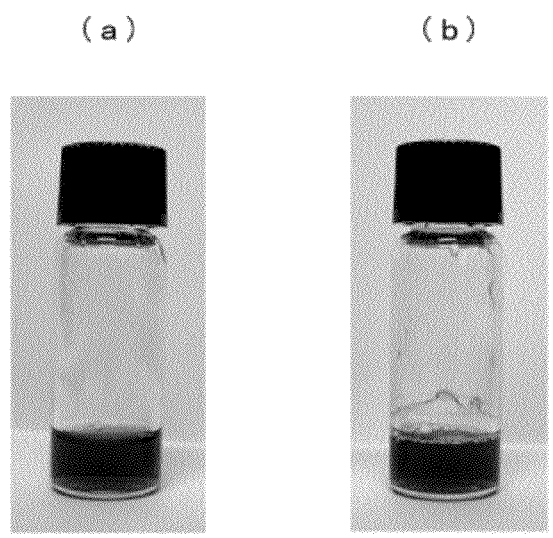
FIG. 5

The experiment was carried out as described below. First, cultured HeLa cells were seeded in a 35 mm dish and incubated under a condition of 37° C. and 5% $CO_2$ until the HeLa cells reached 80% confluency. Next, (1) the $C_{70}$-incorporated liposome solution, (2) the $C_{60}$-incorporated liposome solution, or (3) a liposome solution was added to the dish so that a lipid concentration was 50 μM. Then, the dish was incubated for 24 hours. After the incubation, in order to remove unincorporated liposomes, a culture medium was removed from the dish by aspiration and then the dish was washed 3 times with 1 ml of Phosphate Buffer Saline (PBS) whose temperature had been warmed to 37° C. Further, 2 ml of culture medium whose temperature had been warmed to 37° C. was added to the dish, thereby obtaining samples for light irradiation. The dish containing the samples was then placed in a 35° C. incubator, and subjected to light irradiation for 30 minutes at a wavelength within a range of 400 nm to 800 nm. The culture medium was removed from the dish after the light irradiation, and thereafter, 100 μl of Annexin V-Propidium Iodide solution was added to a cover glass. After the cover glass was allowed to stand for 15 minutes in a dark place, the cover glass was washed with 1×PBS (once with 500 μl). Further, 100 μl of fluorescent dye solution was added to the cover glass, and the cover glass was allowed to stand for 15 minutes in a dark place. After that, the cover glass was washed with 1×PBS (once with 500 μl). The cover glass was then put over a slide glass so that stained cells were sandwiched between the cover glass and the slide glass, thereby obtaining a sample for observation. The sample was observed under a microscope. FIG. 4 shows the result. Images in the upper row of FIG. 4 are phase-contrast images, in which all the cells are observable. On the other hand, images in the lower row of FIG. 4 are of the cells stained with propidium iodide observed under a fluorescence microscope, in which images dead cells are observable. That is, by comparing the images in the upper row of FIG. 4 with those in the lower row of FIG. 4, it is possible to evaluate how many cells among all the cells are dead.

As shown in FIG. 4, few dead cells were observed in the case where (3) the cells were treated with the liposome solution (described as "CO" in FIG. 4). Further, the dead cells were observed in the case where (2) the cells were treated with the $C_{60}$-incorporated liposome solution; however, a percentage of the dead cells with respect to all the cells was extremely low (5%). In contrast, a large number of dead cells were observed in the case where (1) the cells were treated with the $C_{70}$-incorporated liposome solution. In this case, the percentage of the dead cells with respect to all the cells was almost 100%, which was much higher than the case where (2) the cells were treated with the $C_{60}$-incorporated liposome solution.

The experiment revealed that the $C_{70}$-incorporated liposome has a much higher ability of killing cells (cell-killing ability) than the $C_{60}$-incorporated liposome.

Reference Example 1

An aqueous solution of the $C_{70}$-incorporated liposome was produced in the same manner as in Example 1, except that the $C_{70}$ γ-cyclodextrin complex solution was heated and stirred at 80° C. for 2 hours after addition of the lipid solution.

The result was as follows. There was no precipitate (deposit) observed for the aqueous solution of the $C_{70}$-incorporated liposome produced in Example 1 as shown in (a) of FIG. 5, whereas the precipitate (deposit) was attached on an inside surface of a sample bottle for the aqueous solution of the $C_{70}$-incorporated liposome produced in Reference Example 1 as shown in (b) of FIG. 5.

Figure 6:
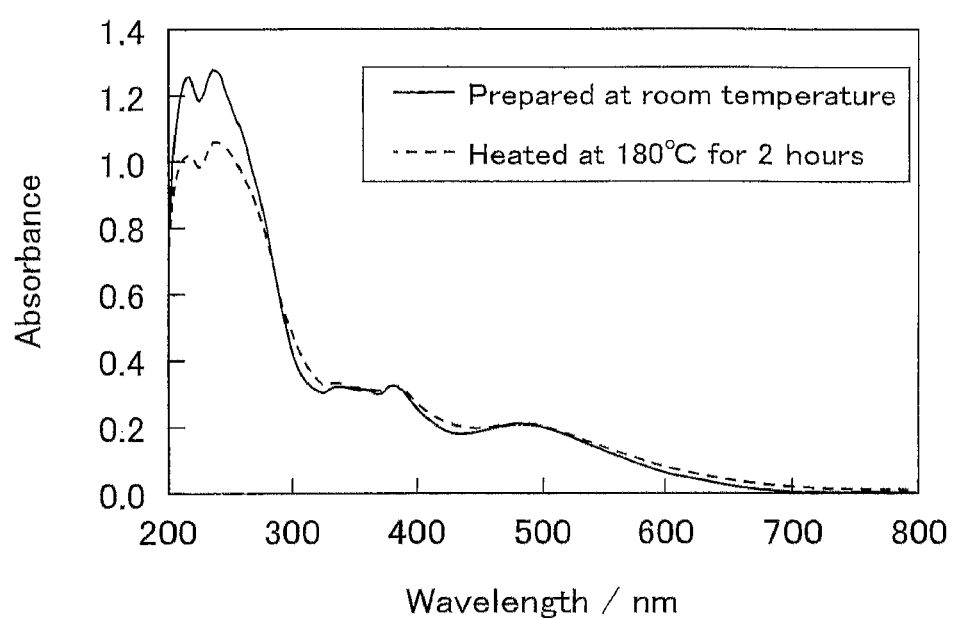
FIG. 6

Further, the UV-vis absorption spectra were measured with use of the aqueous solution of the $C_{70}$-incorporated liposome produced in Example 1 and the aqueous solution of the $C_{70}$-incorporated liposome produced in Reference Example 1. FIG. 6 shows the results. In FIG. 6, the solid line indicates the absorption spectrum of the aqueous solution of the $C_{70}$-incorporated liposome which was prepared at room temperature (the aqueous solution of the $C_{70}$-incorporated liposome produced in Example 1), and the dotted line indicates the absorption spectrum of the aqueous solution of the $C_{70}$-incorporated liposome which was prepared by being heated and stirred at 80° C. for 2 hours (the aqueous solution of the $C_{70}$-incorporated liposome produced in Reference Example 1).

As shown in FIG. 6, an increase of 0.010 in absorbance due to light scattering was observed at 800 nm for the aqueous solution of the $C_{70}$-incorporated liposome produced in Reference Example 1. This indicates that the $C_{70}$-incorporated liposomes were fused with one another to grow into a large $C_{70}$-incorporated liposome. In other words, the $C_{70}$-incorporated liposome produced through a method of Reference Example 1 was found to have a larger average particle diameter than the $C_{70}$-incorporated liposome produced through a method of Example 1. Further, a broadening of a peak absorbance of $C_{70}$ was observed for the aqueous solution of the $C_{70}$-incorporated liposome produced in Reference Example 1. This indicates that association of the $C_{70}$ was in progress. That is, the $C_{70}$ was found to be likely to precipitate in the method of Reference Example 1. Furthermore, decreases in the peak absorbance at 220 nm and 245 nm were observed for the aqueous solution of the $C_{70}$-incorporated liposome produced in Reference Example 1. This indicates that a $C_{70}$ concentration within a system, i.e., an amount of $C_{70}$ incorporated in the $C_{70}$-incorporated liposome, decreased due to the precipitate (deposit) of the $C_{70}$. To sum up, the $C_{70}$-incorporated liposome produced through the method of Reference Example 1 was found to have a low photoactivity.

The invention is not limited to the description of the embodiments above, but may be altered within the scope of the claims. An embodiment based on a proper combination of technical means disclosed in different embodiments is encompassed in the technical scope of the invention. In addition, all the citations stated in the description are incorporated herein by reference.

As described above, the $C_{70}$-incorporated liposome according to the present invention is in a state in which a $C_{70}$ fullerene is incorporated in a liposome. Therefore, the present invention makes it possible to stably solubilize the $C_{70}$ fullerene to a polar solvent while keeping original physical properties of the $C_{70}$ fullerene. Further, the method according to the present invention for producing the $C_{70}$-incorporated liposome makes it possible to produce the $C_{70}$-incorporated liposome through a simple process, wherein a first solution containing a $C_{70}$ cyclodextrin complex and a second solution containing a lipid that is capable of forming a liposome are mixed with each other at a temperature in a range of 10° C. to 45° C. Accordingly, the method according to the present invention makes it possible to quickly produce, without necessity of a particular equipment, a $C_{70}$-incorporated liposome that is soluble in a polar solvent.

The embodiments discussed in the foregoing description of embodiments and concrete examples serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

Industrial Applicability

The present invention makes it possible to solubilize $C_{70}$ to an aqueous solvent without sacrificing its function by incorporating the $C_{70}$ into a liposome. Accordingly, the present invention is applicable not only in PDT medicines, bactericides, cosmetics and the like, but also in a wide range of fields such as pharmaceutical chemical fields, material chemical fields, and electrochemical fields.

The invention claimed is:

1. A method for producing a liposome in which a $C_{70}$ fullerene is incorporated,
the method comprising the step of:
mixing a first solution and a second solution together at a temperature in a range of 10° C. to 45° C., the first solution containing a $C_{70}$ cyclodextrin complex and the second solution containing a lipid with which a liposome is formable.

2. The method for producing a $C_{70}$-incorporated liposome according to claim 1, wherein the $C_{70}$ cyclodextrin complex is at least one of a $C_{70}$ cyclodextrin complex selected from the group consisting of: a $C_{70}$ β-cyclodextrin complex, a $C_{70}$ γ-cyclodextrin complex, a $C_{70}$ δ-cyclodextrin complex, a $C_{70}$ ε-cyclodextrin complex, and a complex between a mono-, di-, or tri-methylated form of β-cyclodextrin, γ-cyclodextrin, δ-cyclodextrin or ε-cyclodextrin and a $C_{70}$ fullerene.

3. The method for producing a $C_{70}$-incorporated liposome according to claim 1, wherein the second solution contains at least one lipid selected from the group consisting of lipids represented by the following general formulas (1) to (3):

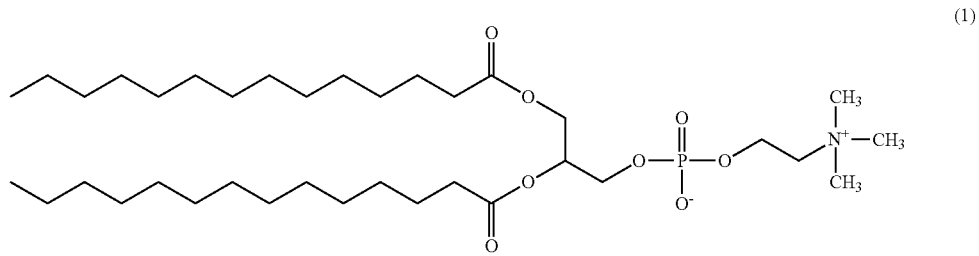

(1)

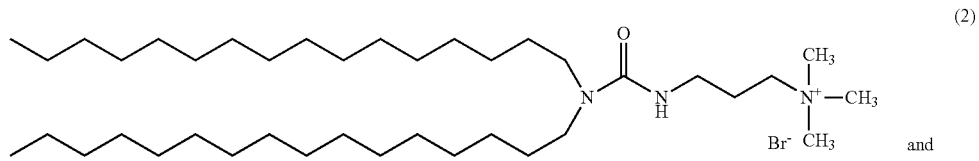

(2)

and

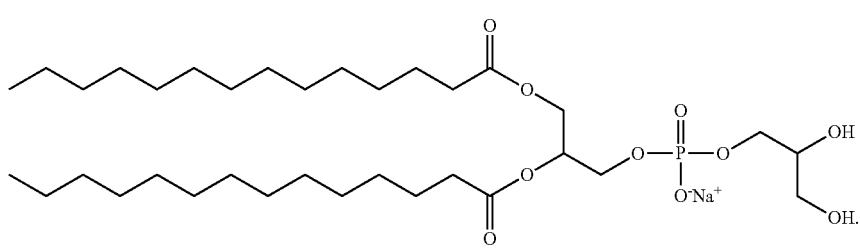
(3)
\* \* \* \* \*